(12) United States Patent
Thorne et al.

(10) Patent No.: US 9,320,800 B2
(45) Date of Patent: Apr. 26, 2016

(54) METHODS AND COMPOSITIONS FOR ENHANCING INTRANASAL DELIVERY OF THERAPEUTIC AGENTS

(71) Applicant: Wisconsin Alumni Research Foundation, Madison, WI (US)

(72) Inventors: Robert Gary Thorne, Madison, WI (US); Jeffrey James Lochhead, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/967,089

(22) Filed: Aug. 14, 2013

(65) Prior Publication Data

US 2014/0050718 A1 Feb. 20, 2014

Related U.S. Application Data

(60) Provisional application No. 61/683,549, filed on Aug. 15, 2012.

(51) Int. Cl.
| | |
|---|---|
| A61K 47/42 | (2006.01) |
| A61K 38/43 | (2006.01) |
| A61K 38/48 | (2006.01) |
| A61K 9/00 | (2006.01) |
| A61K 45/06 | (2006.01) |
| A61K 39/395 | (2006.01) |

(52) U.S. Cl.
CPC ............... *A61K 47/42* (2013.01); *A61K 9/0043* (2013.01); *A61K 38/43* (2013.01); *A61K 38/4886* (2013.01); *A61K 39/395* (2013.01); *A61K 45/06* (2013.01); *A61K 9/0085* (2013.01)

(58) Field of Classification Search
CPC ... A61K 9/0043; A61K 39/365; A61K 38/43; A61K 47/42; A61K 45/06
USPC .............................. 424/130.1, 94.67; 435/219
See application file for complete search history.

(56) References Cited

U.S. PATENT DOCUMENTS

2004/0234499 A1* 11/2004 Shealy et al. ................. 424/85.1

OTHER PUBLICATIONS

Watanabe H et al. (1993). Matrix Metalloproteinase-9 (92 kDa gelatinase/type IV collagenase) from U937 monoblastoid cells: correlation with cellular invasion. Journal of Cell Science, v104, p. 991-999.*
Gigliotti F et al. (2002). Passive Intranasal Monoclonal Antibody Prophylasis against Murine Pneumocystis carinii Pneumonia. Infection and Immunity, v70(3), p. 1069-1074.*
Illum L. (2002). Nasal drug delivery: new developments and strategies. DDT, v7(23), p. 1184-1189.*
Illum (2012). Nasal Drug Delivery—Recent developments and future prospects. Journal of Controlled Release, v161, p. 254-263.*
Miller (1995). Targeted vectors for gene therapy. FASEB J., vol. 9, pp. 190-199.*
Deonarain (1998). Ligand-targeted receptor-mediated vectors for gene delivery. Expert Opin. Ther. Pat., vol. 8, pp. 53-69.*
Verma (1997). Gene therapy—promises, problems and prospects. Nature, vol. 389, pp. 239-242.*
Crystal (1995). Transfer of Genes to Humans: Early Lessons and Obstacles to Success. Science, vol. 270, p. 404-410.*
Pfeifer (2001). Gene Therapy: Promises and Problems. Annu. Rev. Genomics. Hum. Genet., vol. 2, p. 177-211.*
Johnson-Saliba (2001). Gene Therapy: Optimising DNA Delivery to the Nucleus. Curr. Drug. Targets, 2001, vol. 2, p. 371-399.*
Shoji (2004). Current Status of Delivery Systems to Improve Target Efficacy of Oligonucleotides. Current Pharmaceutical Design, vol. 10, p. 785-796.*
Devalia et al (1990). Culture and comparison of human bronchial and nasal epithelial cells in vitro. Respiratory Medicine, 84(4), p. 303-312.*
Limber et al. (1952). Enzymatic Lysis of Respiratory Secretions by Aerosol Trypsin. JAMA, v149(9), p. 816-821.*
Deli (2009). Potential use of tight junction modulators to reversibly open membranous barriers and improve drug delivery. Biochimica et Biophysica Acta, v1788, p. 892-910.*
Tochowicz et al. (2007). Crystal Structures of MMP-9 Complexes with Five Inhibitors: Contribution of the Flexible Arg424 Side-chain to Selectivity, J Mol Biol, v371(4), p. 989-1006.*
Goldblum et al. (2011). The active Zot domain (aa 288-293) increases ZO-1 and myosin 1C serine/threonine phosphorylation, alters interaction between ZO-1 and its binding partners, and induces tight junction disassembly through proteinase activated receptor 2 activation. FASEB Journal, v25, p. 144-158.*
Legrand et al. (1999). Airway Epithelial Cell Migration Dynamics: MMP-9 Role in Cell—Extracellular Matrix Remodeling. JCB, v146(2), p. 517-529.*
Hokosawa et al. (epub May 2011). Increased serum matrix metalloproteinase-9 in neuromyelitis optica: Implication of disruption of blood-brain barrier. Journal of Immunology, v236, p. 81-86 plus appended Pubmed Abstract for epub date.*
Feng et al. (Aug. 17, 2011). Matrix Metalloproteinase-2 and -9 Secreted by Leukemic Cells Increase the Permeability of Blood-Brain Barrier by Disrupting Tight Junction Proteins. PLoS One, v6(8), e20599, 11 pages.*
Internet article Neural Repair Institute (2007). 6 pages plus screen capture for pub. date.*
Vines R.R., et al., "Fragilysin, the enterotoxin from Bacteroides fragilis, enhances the serum antibody response to antigen co-administered by the intranasal route", Vaccine (2000) vol. 19, No. 6, pp. 655-660; Elsevier Ltd., GB.
Lochhead, J.J., et al., "Intranasal Delivery of Biologics to the Central Nervous System", Advanced Drug Delivery Reviews (2012) vol. 64, No. 7.
Vermeer, P.D. et al., "MMP9 Modulates Tight Junction Integrity and Cell Viability in Human Airway Epithelia", American Journal of Physiology, Lung Cellular and Molecular Physiology (2009) vol. 296, No. 5.
Zhang, X, et al., "Current Advances in Vehicles for Brain Gene Delivery", Current Gene Therapy (2012) vol. 12, No. 5, Bentham Science Publishers Ltd., Netherlands.
Lochhead, J.J., et al., "Matrix Metalloproteinase-9 Increases Rapid Delivery of Macromolecules to the Brain Following Intranasal Administration", Abstracts of the Annual Mtg. of Society for Neuroscience (2012) vol. 42 (abstract only), Society for Neuroscience, Washington, DC.
International Searching Authorty, "International Preliminary Report on Patentability and Written Opinion of the International Searching Authority," with respect to PCT/US2013/055066 dated Aug. 15, 2012.

* cited by examiner

*Primary Examiner* — Scott Long
*Assistant Examiner* — Sean C Barron
(74) *Attorney, Agent, or Firm* — Quarles & Brady, LLP

(57) ABSTRACT

A method for treating a patient suffering from a condition with an active compound comprising the steps of (a) treating the patient intranasally with an effective amount of MMP-9 or a functionally equivalent fragment, wherein the tight junctions of the patient's nasal epithelial cells are modulated or wherein the basal lamina of the patient is partially digested and type IV collagen of the patient is degraded or wherein access to the patient's perineural, perivascular, or lymphatic compartment spaces is facilitated and (b) treating the patient intranasally with an active compound is disclosed.

13 Claims, 18 Drawing Sheets
(16 of 18 Drawing Sheet(s) Filed in Color)

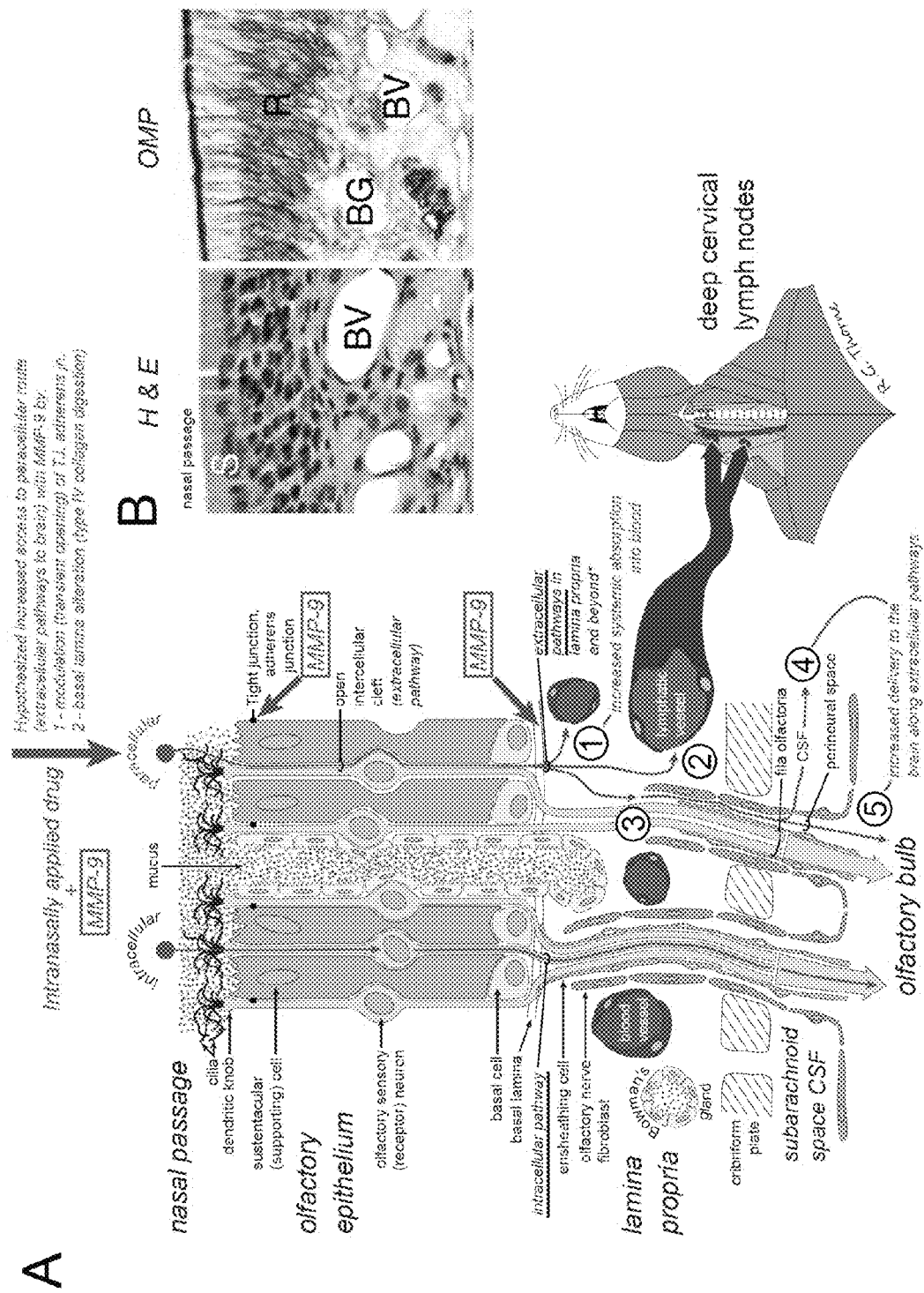
Figure 1 A & B

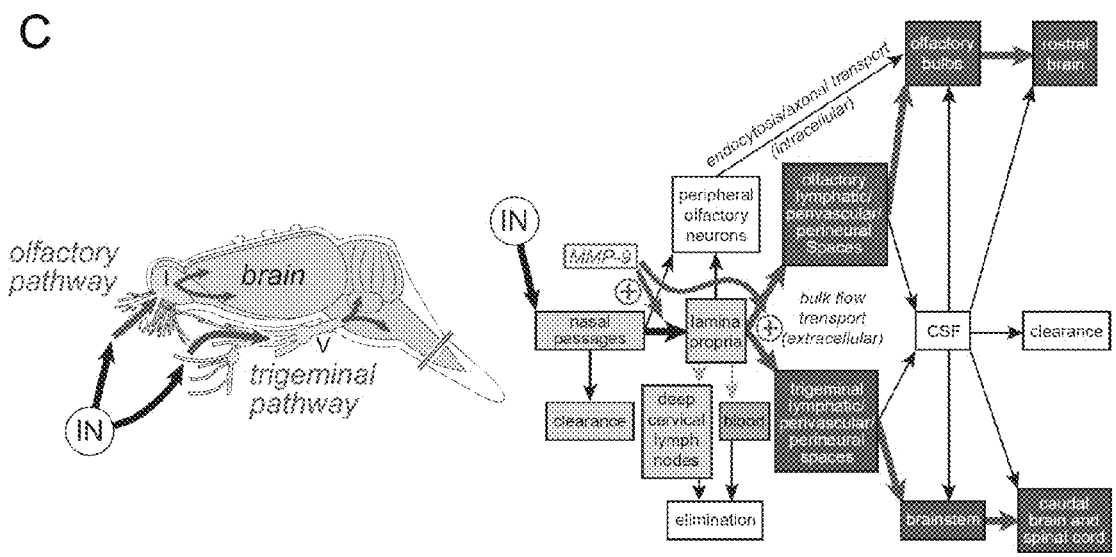
Figure 1 - C

Figure 5 - A to D

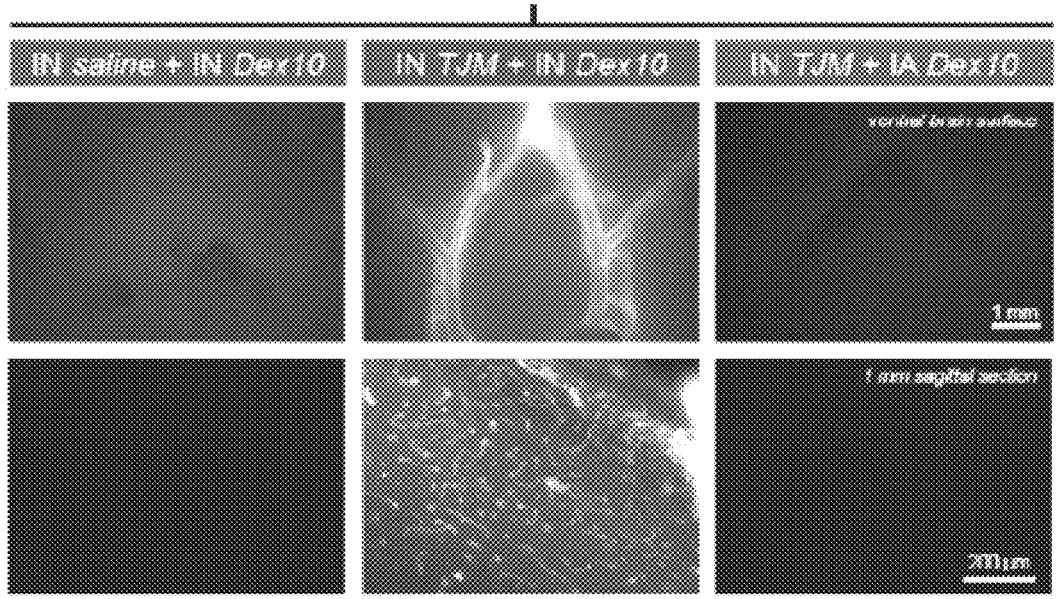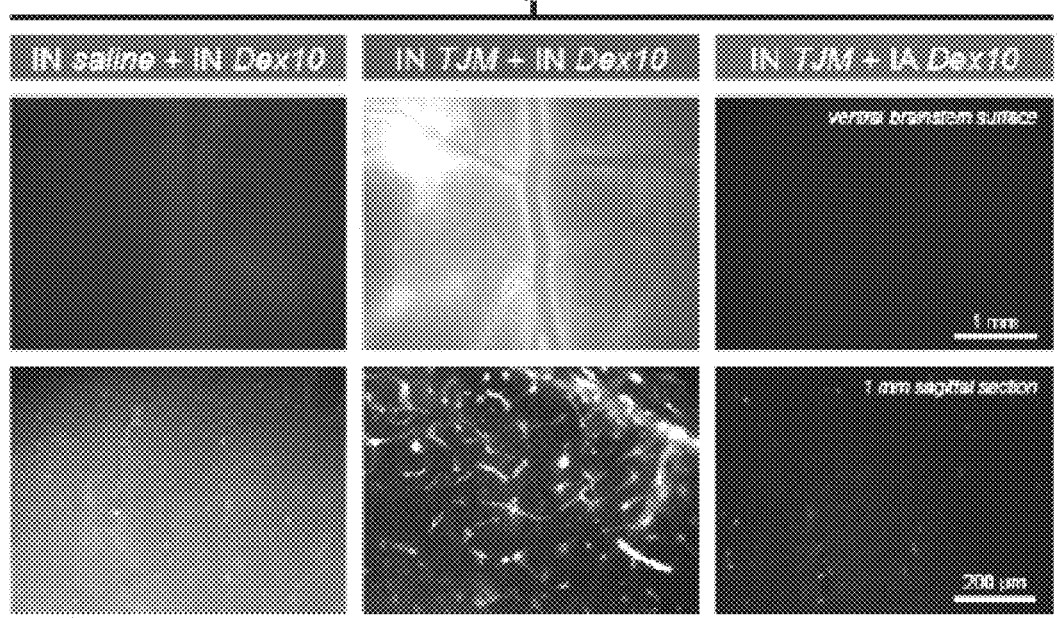
Figure 8

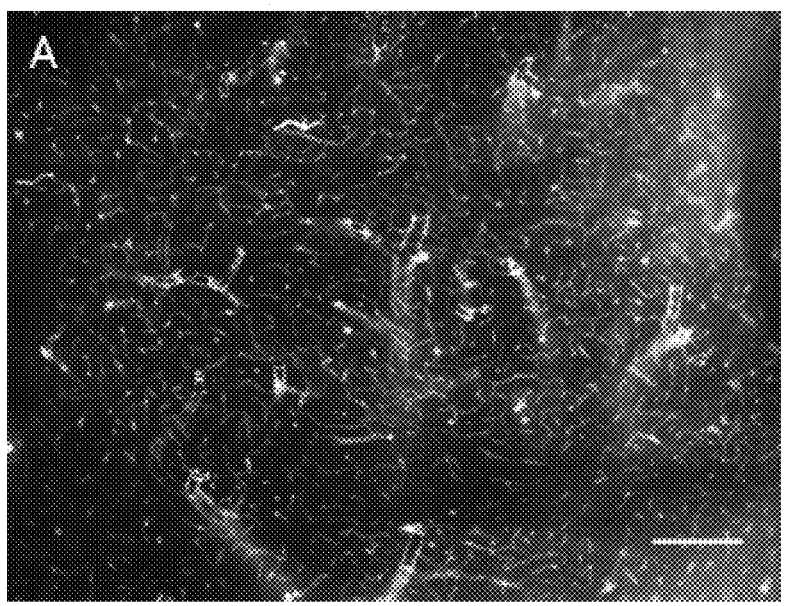
Figure 11

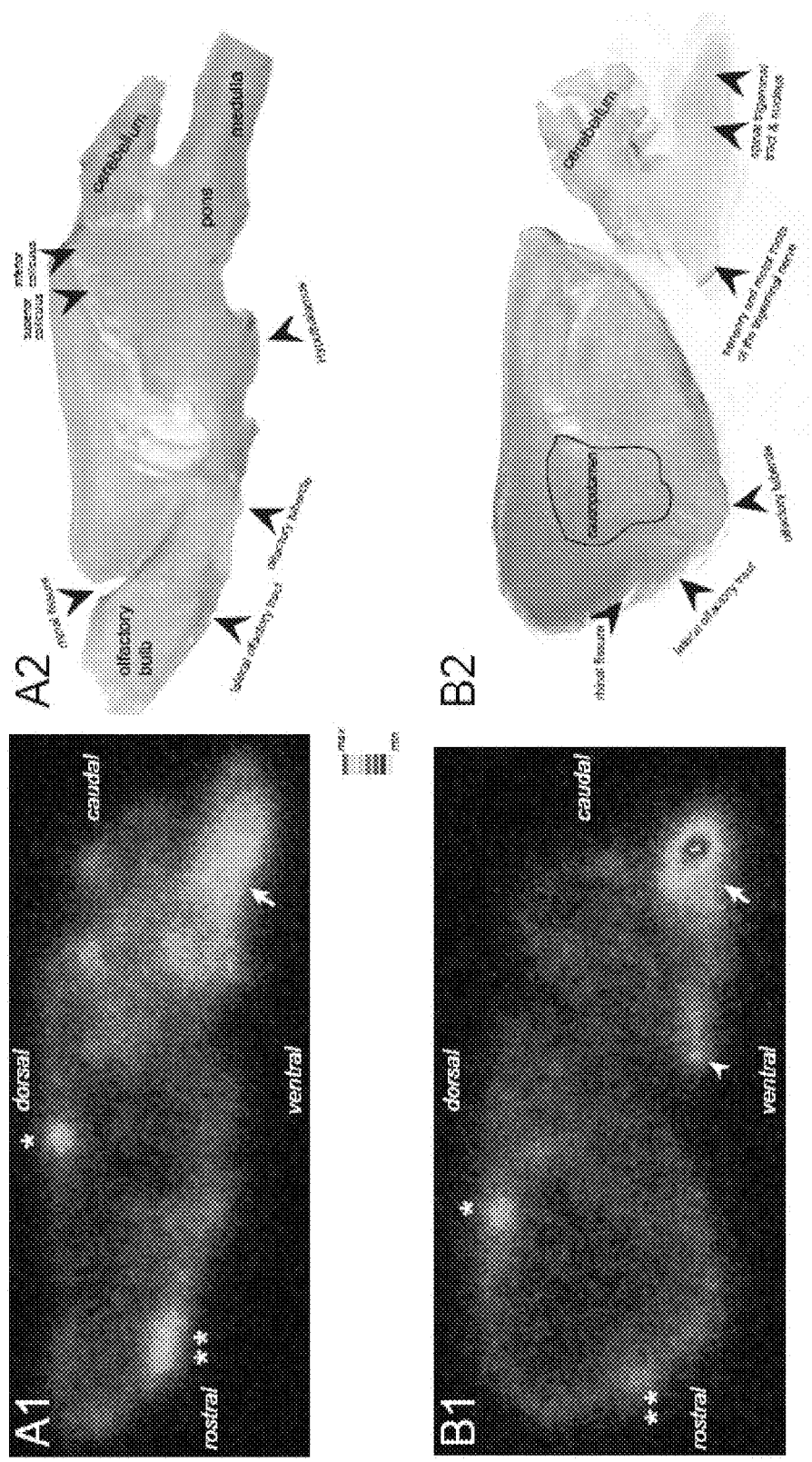
Figure 13 - A, B

A0 *Rat brain atlas schematic (adapted from Paxinos & Watson, 2007)*
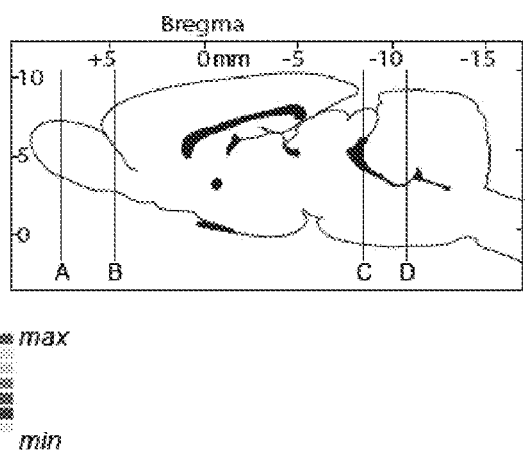
max
min
A1 *Olfactory bulb dorsal*
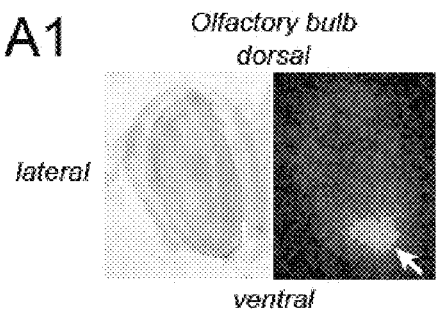
lateral — medial
ventral
A2 *Olfactory bulb dorsal*
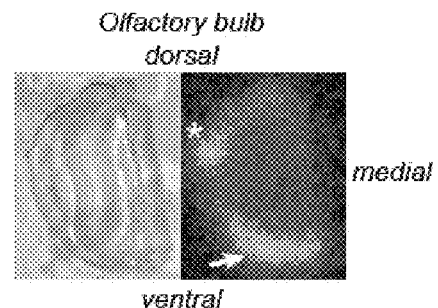
lateral — medial
ventral
Figure 14 - A

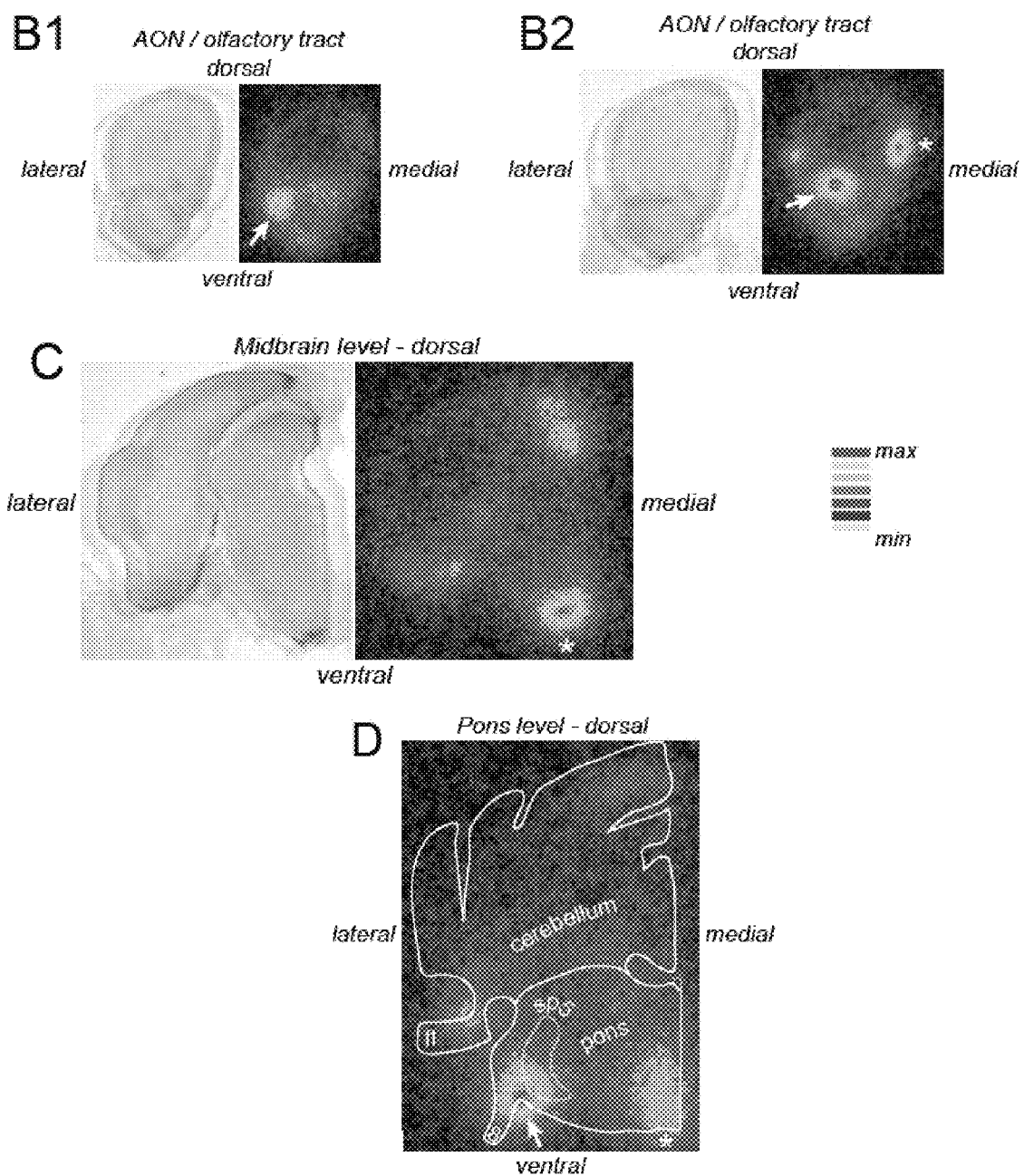
Figure 14 - B to D

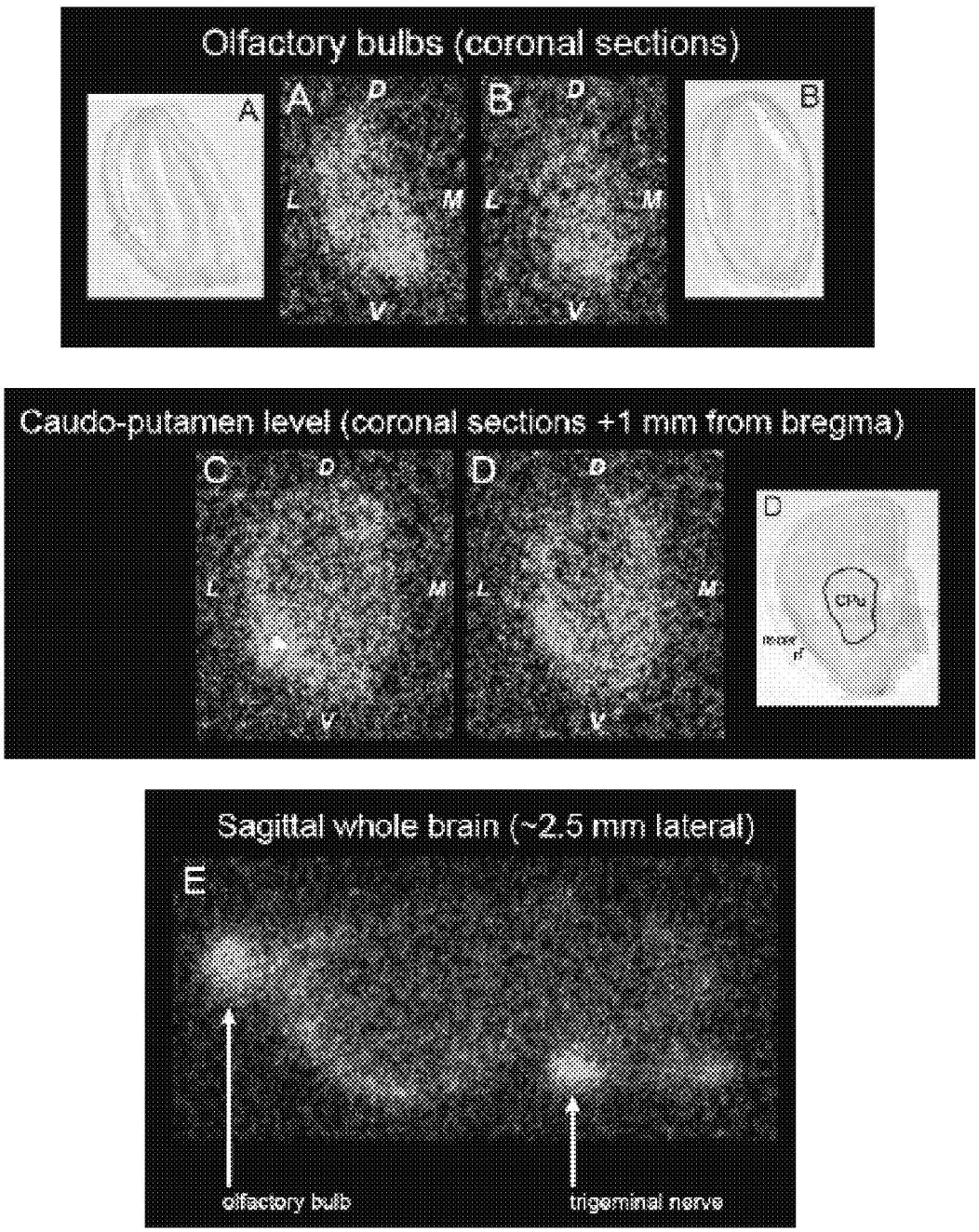
Figure 15 - A to E

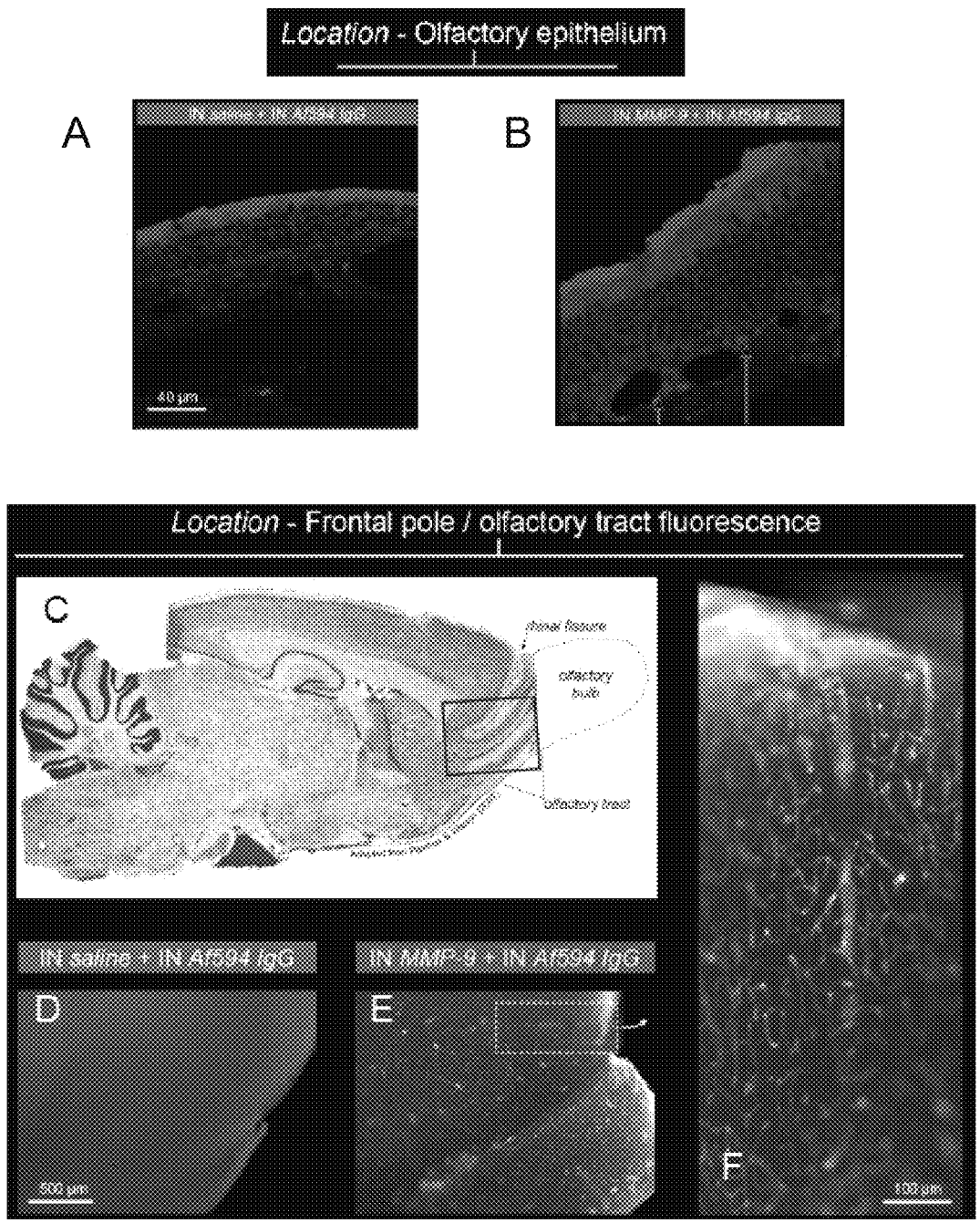
Figure 16 - A to F

METHODS AND COMPOSITIONS FOR ENHANCING INTRANASAL DELIVERY OF THERAPEUTIC AGENTS

CROSS-REFERENCE TO RELATED APPLICATIONS

This application claims benefit from U.S. Provisional Application 61/683,549, filed Aug. 15, 2012. This application is incorporated herein by reference for all purposes.

STATEMENT REGARDING FEDERALLY SPONSORED RESEARCH

N/A

BACKGROUND

Intranasal administration of medicines for symptomatic relief and prevention of topical nasal conditions has been widely used. However, recently the nasal mucosa has emerged as a therapeutically viable route for drug delivery into the brain as well as systemically. Therapeutics delivered by this route include small molecules such as estradiol, sumatriptan, fentanyl, and larger molecules like calcitonin. Many factors affect intranasal drug absorption including size of the molecule, hydrophobicity, and charge. There has been a lot of effort to enhance absorption across the nasal epithelium using excipients that aid permeation. However, most absorption/permeability enhancers used over the past several decades to modify epithelial and endothelial junctional complexes and enhance paracellular permeability have suffered from poorly defined modes of action and substantial toxicity at active concentrations (Hillery, Lloyd, et al., 2001; Ilium, 2012).

The cells in the nasal epithelium connect to one other through regions called tight junctions (TJ). The complexity and tissue-specific nature of TJ components and their organization has presented a further challenge to the development of effective enhancers because modes of action may vary markedly between tissue sites. Modulator substances used to increase nasal epithelial permeability to intranasally applied drugs and tracers have included calcium chelators (e.g. EGTA), bile salts, cyclodextrins, nitric oxide donors, and other chemicals (Deli, 2009). However, none of these are clinically used at present with approved/marketed nasal peptide or protein drugs (e.g. calcitonin, desmopressin, buserelin, nafarelin, and oxytocin) due to historically poor patient tolerability, associated irreversible damage to epithelial cells, or other toxicity (Hillery, Lloyd, et al., 2001; Ilium, 2012). The identification and development of new modulator substances based on endogenous molecules has much potential.

Physiologic processes such as re-epithelialization (where cell migration into a damaged epithelium is facilitated by modification of TJ and extracellular matrix (ECM) components) are known to involve secreted protein modulators with high potency that act transiently and can even be "turned off" by other endogenous substances. There is a great deal of interest in discovering and developing new modulators.

We have focused on one such group of potential modulator substances, the gelatinase subclass of matrix metalloproteinases (MMPs). Matrix metalloproteinases consist of a large multigene family of well over 20 zinc-dependent endopeptidases. Although originally named for their ability to degrade extracellular matrix components, MMPs are now recognized to serve diverse roles in epithelial migration, blood-brain barrier modification in neurodegenerative diseases and stroke, and tumor progression (Bauvois, 2012; Chen and Parks, 2009; Rosenberg, 2009; Rosenberg, 2012; Rosenberg, Estrada, et al., 1998; Roy, Yang, et al., 2009). Importantly, MMPs have been identified in the normal olfactory epithelium of rodents, where they are believed to play a role in the turnover of olfactory basal cells and the development of olfactory sensory neurons (Tsukatani, Fillmore, et al., 2003).

The MMPs have commonly been divided into five distinct subclasses based on structural properties and anticipated functions (Maskos and Bode, 2003): collagenases (MMP-1, -8 and -13), gelatinases (MMP-2 and -9), matrilysins (MMP-7 and -26) and stromelysins (MMP-3 and—10). Gelatinase A and B, also referred to as MMP-2 and MMP-9, respectively, are endogenous enzymes secreted by epithelial cells under both normal and pathological conditions. MMP-9 and MMP-2 have been shown to disrupt brain endothelial cell tight junctions (TJ) by impairment of constituent proteins ZO-1, claudin-5 and occludin, resulting in increased permeability of the blood-brain barrier (Feng, Cen, et al., 2011). MMP-9 appears to enhance epithelial permeability to tracers by modifying TJ structure, e.g. transepithelial electrical conductance is increased and localization of the TJ proteins claudin-1 and occludin is altered in primary cultures of well-differentiated human airway epithelia following MMP-9 treatment (Vermeer, Denker, et al., 2009). MMP-9 may also enhance nasal epithelial permeability by partial digestion of the basal lamina, specifically by degrading type IV collagen.

Briefly, gelatinases have a number of attributes that suggest to us that gelatinases may make ideal nasal absorption/permeability enhancers: (i) gelatinases appear to facilitate epithelial repair through the promotion of a pro-migratory phenotype, characterized by a transient breakdown of the ECM and disruption of epithelial TJs, (ii) both endogenous tissue inhibitors of MMPs (TIMPs) as well as small molecule synthetic inhibitors of MMPs have been identified, potentially allowing additional control over the duration of gelatinase action, and (iii) their normal presence in the nasal epithelium, albeit at low levels and likely focused in certain areas (e.g. where resident basal cells are actively undergoing mitosis to become either mature olfactory sensory neurons/sustentacular cells in the olfactory epithelium or ciliated/goblet cells in the respiratory epithelium), may render them less toxic and better tolerated than other non-physiological modulator substances.

In general, the present invention is drawn to a method of applying gelatinases, especially Matrix Metalloproteinase-9 (MMP-9), as a modulator substance for enhancing therapeutic intranasal delivery of active compounds.

BRIEF SUMMARY OF THE INVENTION

In one aspect, the present invention relates to a method for treating a patient suffering from a condition in need of treatment with an active compound comprising the steps of a) treating the patient intranasally with an effective amount of MMP-9 or a functionally equivalent fragment, and b) treating the patient intranasally with an active compound. In one embodiment, after the treatment step a) the tight junctions of the patient's nasal epithelial cells are modulated or the basal lamina of the patient is partially digested and type IV collagen of the patient is degraded or access to the patient's perineural, perivascular, or lymphatic compartment spaces is facilitated.

In another aspect, the present invention relates to a therapeutic device comprising a nebulizer, sprayer or dropper charged with a preparation of MMP-9 or a functionally equivalent fragment.

In another aspect, the present invention relates to A method for treating a patient suffering from a condition in need of MMP-9 or a functionally equivalent fragment comprising the steps of a) providing a solution of MMP-9 or a functionally equivalent fragment, and b) treating the patient intranasally with an effective amount of MMP-9 or a functionally equivalent fragment solution, wherein the tight junctions of the patient's nasal epithelial cells are modulated or wherein the basal lamina of the patient is partially digested and type IV collagen of the patient is degraded or wherein the patient's access to perineural, perivascular, or fila olfactoria compartment spaces is facilitated.

In another aspect, the present invention relates to an MMP-9 formulation for intranasal delivery, wherein the formulation comprises MMP-9 or a functionally equivalent fragment.

In another aspect, the present invention relates to a kit for intranasal delivery comprising (1) a container or formulation wherein the container or formulation comprises MMP-9 or a functionally equivalent fragment and (2) means for delivering MMP-9.

DESCRIPTION OF DRAWINGS

The patent or application file contains at least one drawing in color. Copies of this patent or patent application publication with color drawings will be provided by the Office upon request and payment of the necessary fee.

FIG. 1 is a set of diagrams of the general organization of the olfactory region with proposed mechanisms of MMP-9 for enhancing intranasal drug delivery into the systemic circulation or into the brain along with extracellular pathways (adapted from Lochhead and Thorne, 2012). (A) The cross-section image of the olfactory mucosa including the olfactory epithelium and its underlying lamina propria. (B) The cross-section image of the rodent olfactory mucosa stained with hematoxylin and eosin (H & E) or immunostained using an antibody to olfactory marker protein (OMP), a protein present only in mature olfactory sensory neurons and not sustentacular or basal cells. (C) The schematic representation image shows the olfactory and trigeminal pathways for nasal targeting of the central nervous system (left) and the proposed enhancement mechanism of delivery to the lamina propria or facilitation of access to perivascular, perineural or lymphatic pathways to the brain by MMP-9 is indicated (right). Higher drug levels in the lamina propria are expected to result in higher amounts delivered to the blood and/or brain.

FIG. 8 is a set of widespread cerebral perivascular fluorescence images following intranasal (IN) application of Texas Red-labeled 10 kDa dextran (Dex10) after intranasal (IN) or intra-arterial (IA) applications of saline or matrix metalloproteinase-9 (MMP-9; 100 nM) monitored at the locations of circle of Willis (Location B) and basilar artery (Location C).

FIG. 11 is a set of images showing that intranasal co-administration of MMP-9 and fluorescently labeled 10 kDa dextran (dex10) results in widespread perivascular distribution in the brain. Rats were anesthetized with urethane and administered 12 µl drops of dex10 (25 mg/ml) in alternating nares every 5 minutes (48 µl total) with (A) or without (B) MMP-9 (100 nM). 30 min following the first drop, rats were perfused with phosphate buffered saline followed by 4% paraformaldehyde. The brain was removed and 1 mm thick sections were viewed under an Olympus MVX10 fluorescent macro zoom microscope equipped with a Texas Red filter set. Images from the brainstem were acquired with an Orca-flash 2.8 CMOS camera (Hamamatsu) at the same magnification under the same light intensity and exposure time for each treatment group. Scale bar=100 µm.

FIG. 13 is a set of sagittal autoradiograph images showing $^{125}$I-labeled antibody distribution in rat brain after intranasal administration with MMP-9 pretreatment. Intranasal administration of $^{125}$I-labeled non-targeted rat IgG (~60 µg) to rats with intranasal MMP-9 pretreatment (100 nM). Representative sagittal sections (300 µm) at (A) a medial location (closer to the midline) or (B) a lateral location (further from the midline). A1 and B1 are autoradiographs corresponding to the gross sections shown in A2 and B2, respectively. Signal is strongest at the putative brain entry areas from the nasal passages. These images include the ventral olfactory bulb region (double asterisk) and the brainstem areas corresponding to the trigeminal nerve entry zone (arrowhead) and the spinal trigeminal tract/nucleus (arrows). Additional signal is evident throughout the brain, particularly on the dorsal surface of the cerebral cortex (asterisk), presumed to correspond to perivascular space signal associated with blood vessels.

FIG. 14 is a set of coronal autoradiograph images showing $^{125}$I-labeled antibody distribution in rat brain after intranasal administration with MMP-9 pretreatment. A0 is a schematic image of rat brain atlas adapted from Paxinos & Watson, 2007. Intranasal administration of $^{125}$I-labeled non-targeted rat IgG (~60 μg) to rats with intranasal MMP-9 pretreatment (100 nM). Representative coronal sections (300 μm) through the olfactory bulbs (A1 and A2), olfactory tracts (B1 and B2), midbrain (C) or pons (D). For A1 and A2, signal intensity is strongest in the ventral olfactory bulb, near the area of olfactory nerve entry from the nasal passages (arrows). Lateral signal is sometimes seen (asterisk) and presumed to correspond to perivascular space signal associated with cerebral blood vessels. For B1 and B2, signal intensity is highest within the rhinal fissure (arrows), presumed to correspond to perivascular space signal associated with blood vessels. Other surface signals may also correspond to perivascular space signal (asterisk). For C, the strongest signal was observed in the ventromedial area of the midbrain, in the approximate location of the basilar artery (presumed to be perivascular). For D, autoradiograph is compared with superimposed schematic of section. Strongest signal is associated with an area near to the trigeminal nerve root entry (arrow) and the spinal trigeminal tract (sp5) as well as the ventromedial area in the location of the basilar artery (asterisk).

FIG. 15 is a set of autoradiograph images showing that MMP-9 facilitated delivery of intranasally applied [$^{125}$I]-IgG antibody (150 kDa) to the CNS. A and B were observed at olfactory bulbs (coronal sections). C and D were observed at caudo-putamen level (coronal sections+1 mm from bregma). E was observed at sagittal whole brain (~2.5 mm lateral). The autoradiographs were observed following intranasal administration of tracer levels IgG (72 μCi) with intranasal MMP-9 pre-treatment. These observations show widespread delivery of the antibody. The concentrations of the antibody were in the range of about 10 pM to 100 pM approximately 30 minutes after start of administration.

FIG. 16 is a set of images showing that MMP-9 facilitated access to perivascular spaces enhances intranasal delivery of IgG antibody (150 kDa) to the CNS. Alexa-fluor 594-labeled immunoglobulin G (Af594 IgG; 150 kDa) was used as an example of antibodies. Images A and B were observed on the location of olfactory epithelium. Image A showed that in the absence of MMP-9, Af594 IgG was only present in the surface of olfactory epithelium. Image B showed that after the MMP-9 pre-treatment, Af594 IgG was also present inside of the olfactory epithelium. C shows schematic diagram of the location of frontal pole/olfactory tract. D, E and F show fluorescence images on the location of frontal pole/olfactory tract. These observations suggest: (i) bulk flow along cerebral perivascular spaces is at least partly responsible for rapid distribution of macromolecules within the CNS after intranasal administration and (ii) MMP-9 pre-treatment provides a new strategy for non-invasively delivering macromolecules as large as antibodies to the brain. These observations further demonstrate that cerebral perivascular spaces allow macromolecules to directly access the central nervous system and rapidly achieve widespread distribution following intranasal delivery and MMP-9 facilitates the delivery of macromolecules to the central nervous system following intranasal delivery, possibly by increasing the permeability of the nasal epithelial barrier.

DESCRIPTION OF THE INVENTION

In General

Figure 2:
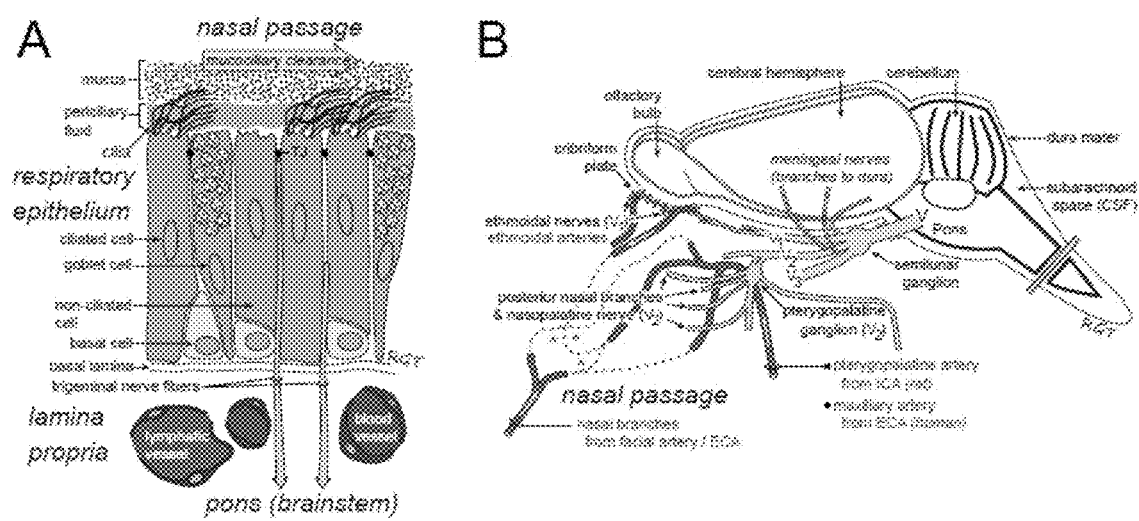
FIG. 2 is a set of illustrations of general organization, trigeminal innervation and vasculature of the nasal respiratory region. (A) The cross-section image of the respiratory mucosa includes the respiratory epithelium and its underlying lamina propria. (B) The schematic image of central projections of the trigeminal nerve shown together with the vasculature of the nasal passage.

Treatment of the central nervous system (CNS) remains a challenging task due to the existence of the blood-brain barrier (BBB). The BBB is located at the level of the cerebral microvasculature, functioning critically for maintaining the central nervous system (CNS) homeostasis. Having a low rate of pinocytosis and tight junctions (TJ), the BBB shows very low permeability, thus greatly restricting paracellular diffusion of solutes from the blood into the brain. Except for some small and non-polar compounds such as lipophilic molecules, the BBB not only restricts the entry of the potential neurotoxic substances into the brain, but also blocks the delivery of nearly all large molecular weight (MW) substances including therapeutic agents into the CNS for disease treatment under normal conditions.

Although there currently exists means such as intraparenchymal, intracerebroventricular, and intrathecal injection/infusion capable of delivering therapeutic agents directly into the CNS, these methods are both invasive (requiring surgery) or likely not practical for chronic drugs that require repeat dosing over time. Consequently, it is of great importance to develop a non-invasive method for the delivery of biologics or other large MW molecules such as antibodies or antibody fragments, peptides, proteins, oligonucleotides, viral vectors, and even stem cells into the CNS. Intranasal (IN) delivery represents one such method. Intranasal administration has been widely used and studied as a drug delivery method that may potentially bypass the BBB to deliver therapeutic agents into the CNS (Lochhead and Thorne, 2012). Although the precise mechanisms and pathways for governing the transportation of molecules from the nasal epithelium to the CNS remain elusive, proposed likely mechanisms and pathways are shown in FIG. 1.

FIG. 1 illustrates the general organization of the olfactory region with proposed mechanisms of MMP-9 for enhancing intranasal drug delivery into the systemic circulation or into the brain along with extracellular pathways (Lochhead and Thorne, 2012). As shown in FIG. 1A, the olfactory mucosa includes the olfactory epithelium and its underlying lamina propria. The olfactory region comprises of <10% of the surface area of the nasal epithelium in man. Axonal processes of olfactory sensory neurons converge into bundles (fila olfactoria), surrounded by ensheathing cells and fibroblasts, before projecting to the olfactory bulb. Still referring to FIG. 1A, potential pathways for drug delivery across the olfactory epithelium following intranasal administration are shown in red. There are two transport pathways including intracellular and extracellular pathways across the "barriers" presented by the olfactory or respiratory epithelia. Intracellular pathways across the olfactory epithelium include endocytosis into olfactory sensory neurons (OSN) and subsequent intraneuronal transport to the olfactory bulb or transcytosis (i.e. transcellular transport) across sustentacular cells to the lamina propria. Extracellular transport pathways across either the olfactory or respiratory epithelia primarily include paracellular diffusion to the underlying lamina propria.

Some substances may be transported by an intracellular pathway from the olfactory epithelium to the olfactory bulb within olfactory sensory neurons following adsorptive, receptor-mediated or non-specific fluid phase endocytosis. Other substances may cross the olfactory epithelial barrier by paracellular or transcellular transport to reach the lamina propria. A number of different extracellular pathways for distribution are possible, including: (1) absorption into olfactory blood vessels and entry into the general circulation; (2)

absorption into olfactory lymphatic vessels draining to the deep cervical lymph nodes of the neck; and (3) extracellular diffusion or convection in compartments associated with olfactory nerve bundles and entry into the cranial compartment.

As shown in FIG. 1A, transport within the perineural space bounded by olfactory nerve fibroblasts is indicated. However, other possibilities of transport exist, such as transport within the fila olfactoria compartment contained by ensheathing cells, transport within the perivascular spaces of blood vessels traversing the cribriform plate with olfactory nerves (not shown), or transport within lymphatics traversing the cribriform plate with olfactory nerves (not shown). Possible pathways for distribution of substances from the perineural space into the olfactory subarachnoid space cerebrospinal fluid (CSF) or into the olfactory bulb are shown in FIG. 1A. Similar pathways are proposed for the nasal respiratory epithelium and trigeminal nerve components (not shown; see Lochhead and Thorne, 2012 for additional details).

As shown in FIG. 1A, tight junctions (TJ) and the lamina propria are involved in the extracellular transport pathways to the brain or into the blood. Substances such as MMP-9 that modulate TJ to provide enhanced access to open intercellular clefts, modify the basal lamina to facilitate increased transport to the lamina propria, and possibly facilitate access to perineural, perivascular, or lymphatic compartment spaces, may thus enhance the intranasal delivery of therapeutic agents.

FIG. 1B shows a cross-section image of the rodent olfactory mucosa stained with hematoxylin and eosin (H & E) or immunostained using an antibody to olfactory marker protein (OMP), a protein present only in mature olfactory sensory neurons and not sustentacular or basal cells. As shown in FIG. 1B, the layers of the olfactory epithelium, positions of the sustentacular (S) cells, olfactory sensory (receptor, R) neurons and the numerous blood vessels (BV) and Bowman's glands (BG) within the lamina propria are visualized in different colors and sections.

FIG. 1C shows a schematic representation of the olfactory and trigeminal pathways for nasal targeting of the central nervous system (left) and a proposed enhancement mechanism of delivery to the lamina propria by MMP-9 is indicated (right). Higher drug levels in the lamina propria are expected to result in higher amounts delivered to the blood and/or brain.

FIG. 2 illustrates general organization, trigeminal innervation and vasculature of the nasal respiratory region. As shown in FIG. 2A, the respiratory mucosa includes the respiratory epithelium and its underlying lamina propria. Fibers of the trigeminal nerve, important for conveying chemosensory, nociceptive, touch, and temperature information, are found throughout the nasal epithelium where their free nerve endings extend nearly to the epithelial surface, just beneath tight junctions (TJ). FIG. 2B are central projections of the trigeminal nerve shown together with the vasculature of the nasal passage. The cell bodies of the trigeminal nerve fibers are located in the semilunar ganglion; their axons project into the brainstem at the level of the pons where they ultimately synapse with neurons in brainstem areas such as the principal sensory and spinal trigeminal nuclei. Of the three main trigeminal nerve divisions (V1, the ophthalmic nerve; V2, the maxillary nerve; and V3, the mandibular nerve), only V1 and V2 send branches to the nasal epithelium. Blood supply to the nasal passages is provided by ethmoidal branches of the ophthalmic artery, sphenopalatine branches of either the external carotid artery (ECA)/maxillary artery (in humans) or the internal carotid artery (ICA)/pterygopalatine artery (in rats), and nasal branches from the ECA/facial artery. Numerous anastomoses (*) connect these branches within the nasal passages.

Figure 3:
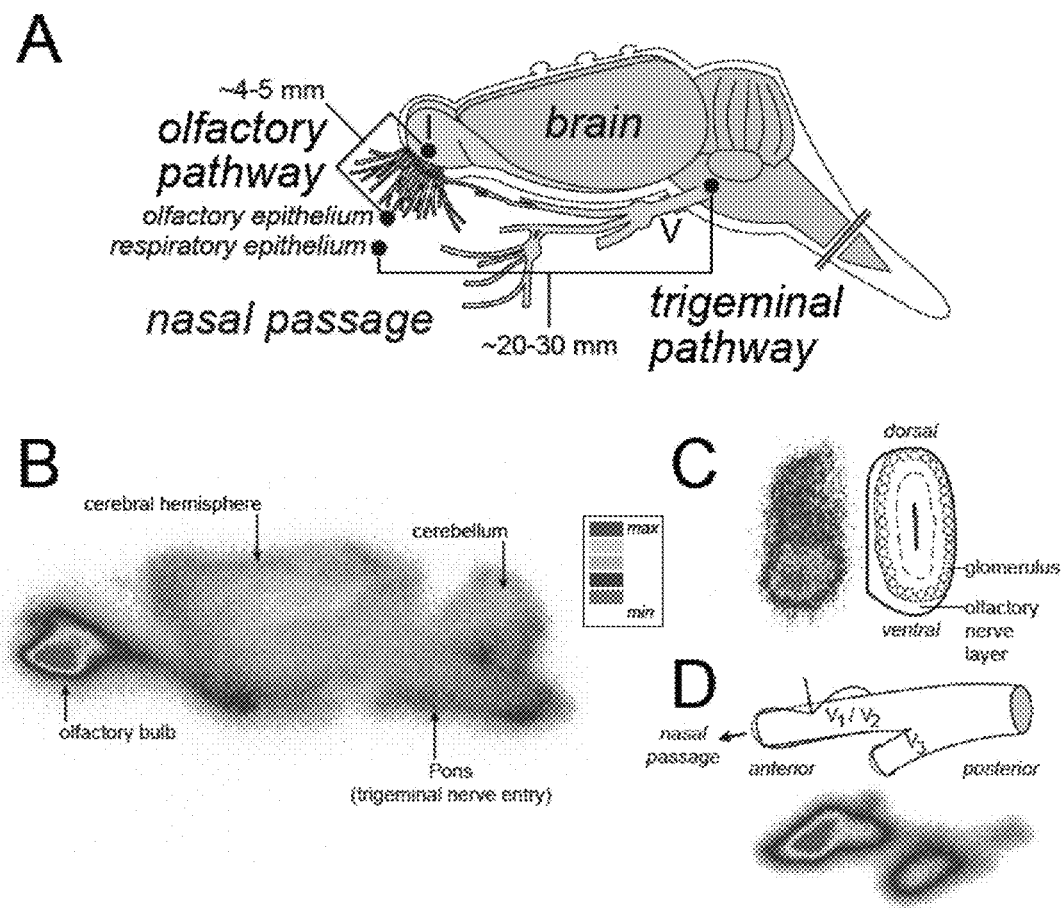
FIG. 3 is a set of diagrams of olfactory and trigeminal-associated pathways appearing to be important for transport of [$^{125}$I]-insulin-like growth factor-I (IGF-I) into the CNS from nasal regions.

FIG. 3 illustrates olfactory- and trigeminal-associated pathways appearing to be important for transport of [$^{125}$I]-insulin-like growth factor-I (IGF-I) into the CNS from nasal regions. As shown in FIG. 3A, there exist two extracellular pathways including an olfactory pathway and a trigeminal pathway for intranasal delivery of IGF-I into the CNS. The olfactory pathway is associated with the peripheral olfactory system connecting the nasal passages with the olfactory bulb and rostral brain regions such as the anterior olfactory nucleus and frontal cortex. The trigeminal pathway is associated with the peripheral trigeminal system connecting the nasal passages with brainstem and spinal cord regions.

FIG. 3B shows representative autoradiograph of a sagittal brain section (2 mm) from a rat following intranasal administration of a very low specific activity [$^{125}$I]-IGF-I solution (0.46 Ci/mmol, 21.2 µCi administered; ratio of unlabeled IGF-I to [$^{125}$I]-IGF-I, 3700:1). As shown in FIG. 3B, Utilizing a very low specific activity solution in the experimental paradigm allows visualization of radiolabel entry into the brain and spinal cord regions from the nasal passages. Specific binding in the CNS is effectively competed off by the presence of unlabeled IGF-I in great excess.

Further, FIG. 3 is a set of representative autoradiographic images of Coronal section (150 µm) through the olfactory bulb (FIG. 3C) and transverse sections (150 µm) through the trigeminal nerve (FIG. 3D) showing signal distribution in different brain regions following intranasal administration of a high specific activity [$^{125}$I]-IGF-1 solution (2100 Ci/mmol, no unlabeled IGF-I present). As shown in FIG. 3C, signal is highest in the ventral olfactory bulb in the area of the olfactory nerve layer of olfactory bulb (ONL), glomerular layer of olfactory bulb (GL) and mitral cell layer of olfactory bulb (MCL). As shown in FIG. 3D, highest signal is observed anteriorly toward the nasal passage (NP) in the V1 and V2 portions of the nerve.

Figure 4:
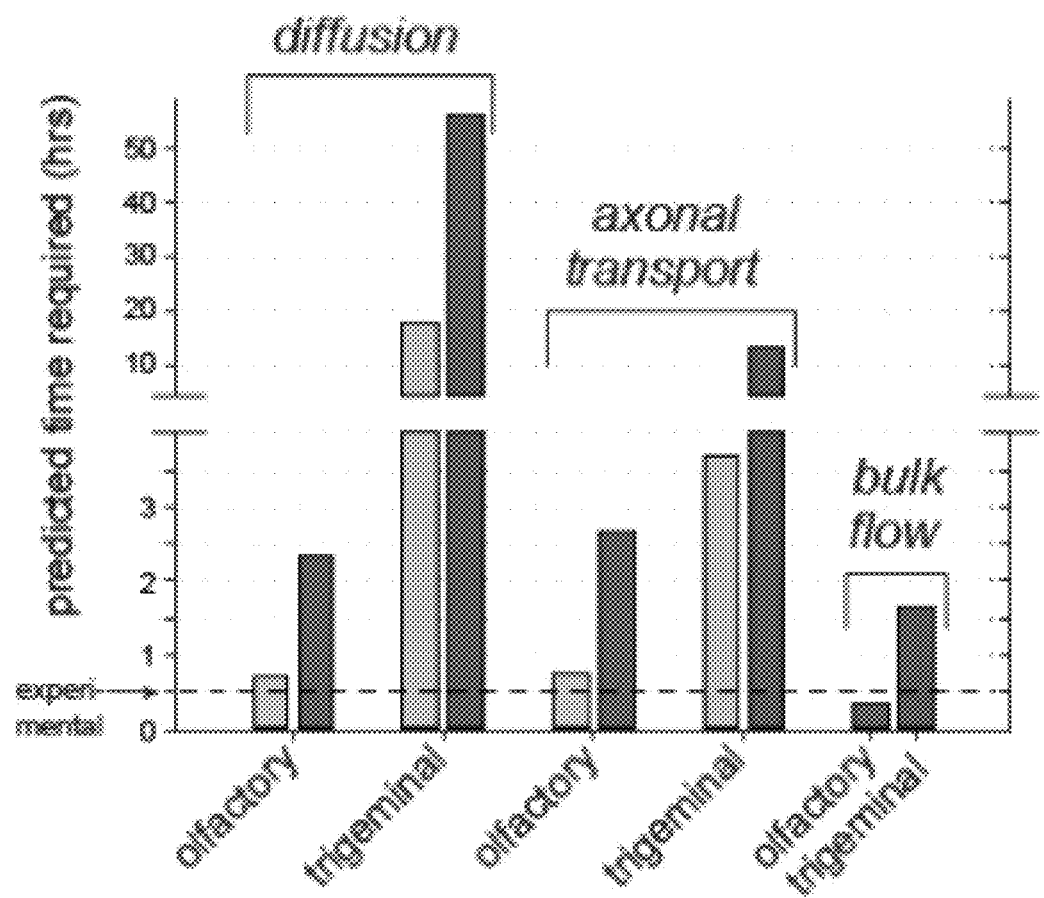
FIG. 4 is a diagram of modeling time predictions for IGF-I transport to the olfactory bulb/brainstem after intranasal administration.

FIG. 4 is a diagram of modeling time predictions for IGF-I transport to the olfactory bulb/brainstem after intranasal administration. Light blue and light red bars represent fast diffusion based on free diffusion coefficient in water; dark blue and dark red bars represent slow diffusion based on effective diffusion coefficient in brain. Intracellular (axonal) transport within olfactory or trigeminal nerves (light blue and light red bars, fast axonal transport based on protein transport rate in olfactory nerves; dark blue and dark red bars, slow axonal transport based on protein transport rate in olfactory nerves) and extracellular convection (bulk flow) along peripheral olfactory or trigeminal components are also depicted.

Figure 5:
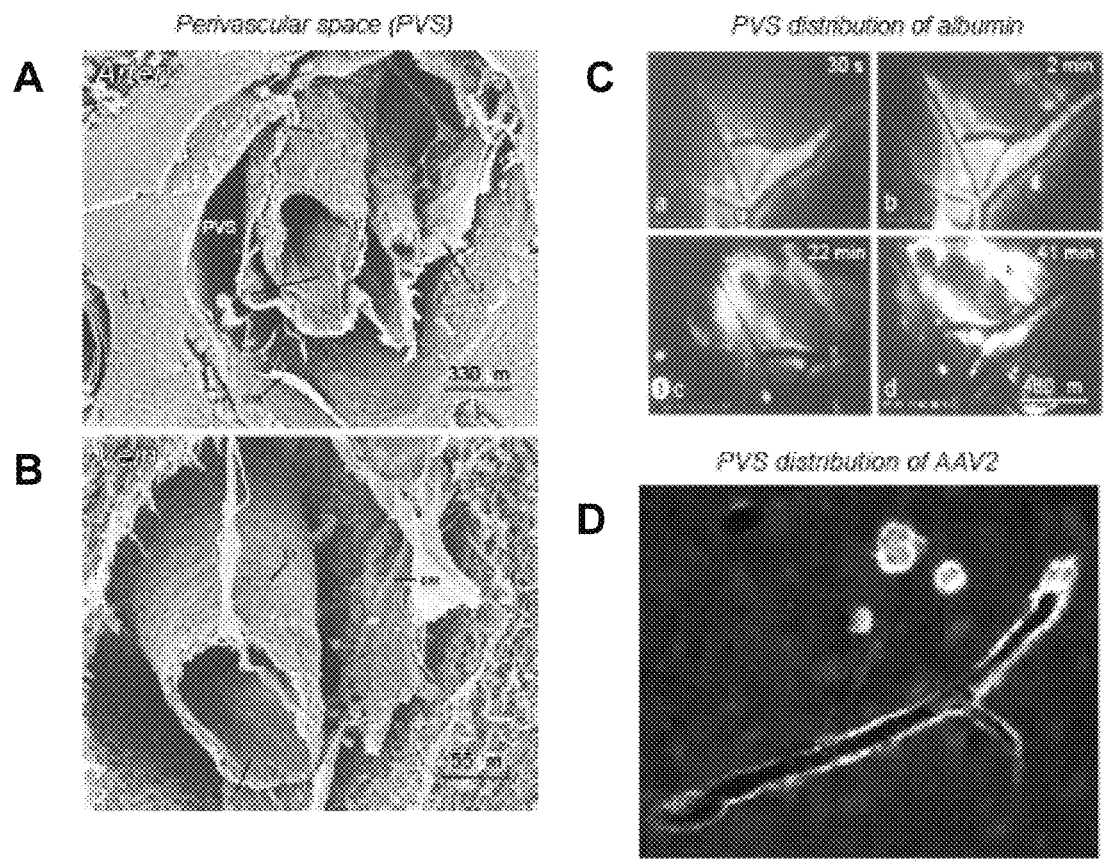
FIG. 5 is a set of images of published evidence suggesting cerebral perivascular spaces can serve as distribution channels for macromolecules after central input.

FIG. 5 illustrates published evidence suggesting cerebral perivascular spaces can serve as distribution channels for macromolecules after central input. For example, perivascular spaces of artery and its branch (left; top) and a vein in the human globus pallidus (left; bottom) are clearly visualized using scanning electron micrographs. Endothelium (E) lines the lumen of the vessel and a layer of cells (L1) coats the outer surface of the vessel. Surrounding the arterial perivascular space is a thin layer of cells (L2) which is separate from the basement membrane (BM). The BM coats the surface of the brain and separates the parenchyma from the PVS. PVS distribution of albumin is depicted after injection of rhodamine-labeled albumin into cortical surface PVS (right; top). PVS distribution of Adeno-associated virus serotype 2 (AAV2) capsid immunoreactivity is also depicted following intrastriatal infusion of AAV2 (right; bottom).

Methods of the Present Invention

In one embodiment, MMP-9 or a functionally equivalent fragment is used as an active compound. The term "effective amount" or "therapeutically effective amount" refers to the amount of MMP-9 or a functionally equivalent fragment that can be delivered to the CNS of a patient for treating a disease condition. In another embodiment, when the MMP-9 or a functionally equivalent fragment is used as an enhancing agent for enhancing intranasal delivery of an active compound, the term "effective amount" or "therapeutically effective amount" refers to the amount of MMP-9 or a functionally equivalent fragment that can effectively enhance intranasal delivery of the active compound.

Treating a disease condition may include one or more of the following: (1) preventing the disease; for example, preventing a disease, condition or disorder in an individual that may be predisposed to the disease, condition or disorder but does not yet experience or display the pathology or symptomatology of the disease; (2) inhibiting the disease; for example, inhibiting a disease, condition or disorder in an individual that is experiencing or displaying the pathology or symptomatology of the disease, condition or disorder (i.e., arresting further development of the pathology and/or symptomatology); and (3) ameliorating the disease; for example, ameliorating a disease, condition or disorder in an individual that is experiencing or displaying the pathology or symptomatology of the disease, condition or disorder (i.e., reversing the pathology and/or symptomatology). Treating a disease condition may also provide a desired therapeutic activity for therapeutic treatment and/or prophylactic treatment, such as, for example, at least partially attaining the desired effect, and/or delaying the onset of, and/or inhibiting the progression of, and/or preventing, halting or reversing altogether the onset or progression of the particular disease, disorder, and/or condition being treated.

As used herein, the term "patient" refers to a human or non-human mammalian patient suffering from a condition in need of treatment.

The term "MMP", as used herein, shall refer to proteases of the matrix metalloproteinase (MMP) family. Proteins of the matrix metalloproteinase (MMP) family are involved in the breakdown of extracellular matrix in normal physiological processes, such as embryonic development, reproduction, Angiogenesis, bone development, wound healing, cell migration, learning and memory, as well as in pathological processes, such as arthritis, intracerebral hemorrhage, and metastasis. Most MMPs are secreted as inactive proproteins which are activated when cleaved by extracellular proteinases. The gelatinase MMPs, including MMP-9 and MMP-2, degrade type IV and V collagens and other extracellular matrix proteins. Studies in rhesus monkeys suggest that the enzyme is involved in IL-8-induced mobilization of hematopoietic progenitor cells from bone marrow, and murine studies suggest a role in tumor-associated tissue remodeling. MMPs play a role in inflammation associated with aortic aneurysms. Doxycycline suppresses the growth of aortic aneurysms through its inhibition of matrix metalloproteinase 9. MMPs such as MMP-9 may be involved in the development of several human malignancies, as degradation of collagen IV in basement membrane and extracellular matrix facilitates tumor progression, including invasion, metastasis, growth and angiogenesis. MMPs, including MMP-9 and other MMPs, have been described previously by Maskos, Bode, et al. (Maskos, Bode et al. 2003).

The term "MMP-9", as used herein, shall refer to matrix metalloproteinase-9 or gelatinase B. For example, Vermeer and coworkers (Vermeer, Denker et al., 2009) disclose MMP-9 molecules suitable for the present invention. In preferred embodiments, one would wish to use a species-identical MMP-9. For human therapies, one would wish to use a human MMP-9 (Van den Steen, Dubois, et al., 2002).

The term "functionally equivalent fragment" refers to a fragment or a modified version of wild type MMP-9 that retains at least 75% activity of the wild type version of MMP-9. In one embodiment, one may wish to use only selected domains of the native MMP-9 protein.

The term "intranasal" or "intranasally", as used herein, refers to a route of delivery of an active compound into the central nervous system or, in some embodiments, into the circulatory system by transporting the compound through the olfactory or respiratory epithelium and the perineural sheet or by axonal transport within olfactory and trigeminal nerves.

The term "active compounds", as used herein, shall refer to any chemical or biological molecules which may be desirable for the patient, for example as used for the treatment of a disease. Examples may include biopharmaceuticals, macromolecules, therapeutic agents, and others. Biopharmaceuticals may include antibodies or antibody fragments, peptides, proteins, vectors for gene therapy (including viral and non-viral vectors), stem cells, and others. Macromolecules may include any oligonucleotide, such as RNA, asRNA, siRNA, DNA, and cDNA. Therapeutic agents may include any other chemicals, such as therapeutic small molecules.

As used herein, the term "nebulizer" or "nebuliser" refers to a drug delivery device used to administer medication in the form of a mist inhaled into the central nervous system through the noses. In one embodiment of the present invention, a nebulizer may be used to intranasally deliver MMP-9 or a functionally equivalent fragment and/or active compounds into the central nervous system of a patient or a subject. Nebulizers may use oxygen, compressed air or ultrasonic power to break up medical solutions and suspensions into small aerosol droplets that can be directly inhaled from the device.

As used herein, the term "aerosol" refers to a mixture of gas and liquid particles, and the best example of a naturally occurring aerosol is mist, formed when small vaporized water particles mixed with hot ambient air are cooled down and condense into a fine cloud of visible airborne water droplets. In one embodiment of the present invention, an aerosol may be produced through an aerosol spray or a sprayer. As used herein, the term "aerosol spray" or "a sprayer" refers to a type of dispensing system which creates an aerosol mist of liquid particles. This is used with a can or bottle that contains a liquid under pressure. When the container's valve is opened, the liquid is forced out of a small hole and emerges as an aerosol or mist. As gas expands to drive out the payload, only some propellant evaporates inside the can to maintain an even pressure. Outside the can, the droplets of propellant evaporate rapidly, leaving the payload suspended as very fine particles or droplets. An atomizer is a similar device that is pressurized by a hand-operated pump rather than by stored gas.

As used herein, the term "antibody(ies)" or "antibody fragments" [synonymous with the term "antibody molecule(s)"] refers to, in the context of the present invention, antibody molecule(s) such as full immunoglobulin molecules, e.g. IgMs, IgDs, IgEs, IgAs or IgGs, like IgGl, IgG2, IgG2b, IgG3 or IgG4 as well as parts of such immunoglobulin molecules, such as Fab-fragments, Fab'-fragments, $F(ab)_2$-fragements, chimeric $F(ab)_2$ or chimeric Fab' fragments, chimeric Fab-fragments or isolated VH— or CDR-regions (said isolated VH- or CDR-regions being, e.g. to be integrated or engineered in corresponding "framework(s)"). Accordingly, the term "antibody" or "antibody fragment" also comprises known isoforms and modifications of immunoglobulins, like single-chain antibodies or single chain Fv fragments (scAB/scFv) or bispecific antibody constructs, said isoforms and modifications being characterized as comprising at least one glycosylated VH region as defined herein. A specific example of such an isoform or modification may be a sc (single chain) antibody in the format VH-VL or VL-VH, wherein said VH comprises the herein described glycosylation. Also bispecific scFvs are envisaged, e.g. in the format VH-VL-VH-VL, VL-VH-VH-VL, VH-VL-VL-VH. Also included in the term "antibody" or "antibody fragments" are diabodies and molecules that comprise an antibody Fc domain as a vehicle attached to at least one antigen binding moiety/peptide, e.g. peptibodies as described in WO 00/24782.

The antibody(ies) or antibody fragments that may be useful in the inventive formulation(s) may be recombinantly produced antibody(ies) or antibody fragments. These may be produced in a mammalian cell-culture system, e.g. in CHO cells. The antibody molecules or antibody fragments may be further purified by a sequence of chromatographic and filtration steps, e.g. in order to purify specifically glycosylated antibody isoforms as described herein below. The term "lyophilizate" as used herein in connection with the formulation according to the invention denotes a formulation which is manufactured by freeze-drying methods known in the art per se. The solvent (e.g. water) is removed by freezing following sublimation under vacuum and desorption of residual water at an elevated temperature. In the pharmaceutical field, the lyophilizate has usually a residual moisture of about 0.1 to 5% (w/w) and is present as a powder or a physical stable cake. The lyophilizate is characterized by dissolution after addition of a reconstitution medium.

As used herein, the term "delivery-enhancing agents" refers to any agents which enhance the release or solubility (e.g., from a formulation delivery vehicle), diffusion rate, penetration capacity and timing, uptake, residence time, stability, effective half-life, peak or sustained concentration levels, clearance and other desired intranasal delivery characteristics (e.g., as measured at the site of delivery, or at a selected target site of activity such as the bloodstream or central nervous system) of MMP-9 or its functionally equivalent fragment or other biologically active compound(s). Enhancement of intranasal delivery can thus occur by any of a variety of mechanisms, for example by increasing the diffusion, transport, persistence or stability of MMP-9 or a functionally equivalent fragment, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

The present invention is generally applied to humans. In certain embodiments, non-human mammals, such as rats, may also be used for the purpose of demonstration. One may use the present invention for veterinary purpose. For example, one may wish to treat commercially important farm animals, such as cows, horses, pigs, rabbits, goats, and sheep. One may also wish to treat companion animals, such as cats and dogs.

In one embodiment, MMP-9 or its functionally equivalent fragment may be obtained from any suitable sources. For example, a human MMP-9 has been previously described by Van den Steen et al. (Van den Steen, Dubois, et al., 2002). One may also obtain MMP-9 from any suitable commercial sources, such as SINO BIOLOGICAL INC. Preferably, a suitable MMP-9 is in a human form.

In one embodiment of the present invention, MMP-9 or its functionally equivalent fragment may be applied intranasally to a patient in a combination with active compounds. The intranasal applications of MMP-9 or its functionally equivalent fragment and active compounds may be simultaneous or the application of the active compound may be subsequent to the application of MMP-9 or its functionally equivalent fragment. When MMP-9 or its functionally equivalent fragment and active compounds are applied intranasally in a subsequent manner, the active compound may be applied any time after the intranasal application of MMP-9 or its functionally equivalent fragment. In one embodiment, the active compound may be applied at any time up to 4 hours after the administration of MMP-9 or its functionally equivalent fragment. In one specific embodiment, the active compounds are preferably applied 5 minutes to 1 hour after the intranasal application of MMP-9 or its functionally equivalent fragment. Preferably, the active compounds are applied within 4 hours after treatment with MMP-9 or its functionally equivalent fragment. In another preferred embodiment, the active compound may be co-administered with MMP-9 or its functionally equivalent fragment.

In the present method, MMP-9 or a functionally equivalent fragment, is typically initially prepared as an aqueous solution, preferably a saline or other buffered solution, having a concentration of about 0.1-10,000 nanomolar (nM), preferably about 1-400 nM, more preferably about 50-400 nanomolar, most preferably between about 1 nM-150 nM. In some embodiments, the concentration will be between 1-1000 nM.

Non-human patients are typically first anesthetized. For human patients, anesthesia, analgesia or sedation of any type is not typically required. The treatment may be performed by patients themselves using either a nasal spray (for example, squeeze bottles, metered dose devices, or special devices such as breath actuated release devices or olfactory epithelium targeting devices) or nasal drops. The Examples below show rats anesthetized with an effective amount of urethane.

The as-prepared MMP-9 or its functionally equivalent fragment solution is then intranasally applied to the patient. In one embodiment, MMP-9 or its functionally equivalent fragment is applied as drops or sprays. In other embodiments, MMP-9 or its functionally equivalent fragment is applied as a powder or a dried or lyophilized form.

Further, to ensure that the patients receive an effective amount of MMP-9 or its functionally equivalent fragment, the MMP-9 or its functionally equivalent fragment solution is preferably intranasally administered to alternating nares. The Examples below show an amount such as 6 μL drops for every certain amount of time, such as for every 5 minutes, delivered to rats. Typically, for human patients, a suitable amount is in the range of 50-100 μL, up to 2.5 mL, of a 1 nM-150 nM solution. This amount is preferably divided into drops applied multiple times, for example two, three, or four times. Preferably, the drops will be applied in five minute intervals.

If one were to use a powder or gas phase of MMP-9 or a functionally equivalent fragment, an equivalent amount of MMP-9 or a functionally equivalent fragment will be applied.

In one embodiment, after the intranasal application of MMP-9 or a functionally equivalent fragment is completed, an active compound is intranasally applied to the patient. In the Examples below, 10 kDa lysine-fixable Texas Red dextran (Dex10) is used as an example due to its fluorescence property. Any active compound may be applied in the present invention. Active compounds such as Dex10 are intranasally applied to the patient in the same manner as that of MMP-9.

Alternatively, MMP-9 or its functionally equivalent fragment and active compounds may be applied intranasally in a simultaneous manner. In one embodiment of the present invention, the as-prepared MMP-9 or its functionally equivalent fragment solution and active compounds are mixed into a mixture solution in the effective amounts. The mixture solution is then intranasally applied to the patient.

In another embodiment of the present invention, MMP-9 or its functionally equivalent fragment may be applied intranasally to a patient without additional active compounds. Due to its unique ability to modulate the tight junctions of the brain endothelial cells, partially digest the basal lamina and degrade type IV collagen, and possibly facilitate access to perineural, perivascular, or fila olfactoria compartment spaces, MMP-9 or its functionally equivalent fragment may be applied as an active compound to treat a related disease. As above, in the present method, MMP-9 is initially prepared as an aqueous solution having a concentration of 1-400 nanomolar (nM). Other concentrations of MMP-9 or its functionally equivalent fragment may also be prepared.

This embodiment of the present invention would be especially useful in the treatment of neurodegenerative diseases such as Alzheimer's disease, Parkinson's disease and Huntington's disease, as well as many other diseases including but not limited to amyotrophic lateral sclerosis, multiple sclerosis, stroke, traumatic brain injury, brain cancer, lysosomal storage disorders, mental disorders (e.g. autism spectrum disorders), epilepsy and neuroAIDS. In diseases such as Alzheimer's, where amyloid aggregates are thought to obstruct perivascular distribution spaces, we predict that intranasal application of MMP-9 will facilitate relief from these obstructions, thereby restoring beneficial normal distribution and clearance of toxic products (e.g. amyloid, alpha-synuclein or other potentially pathological substances).

Compositions of the Present Invention

In one embodiment of the present invention, a composition for enhancing intranasal delivery of active compounds includes a combination of MMP-9 or its functionally equivalent fragment and active compounds prepared for nasal delivery. The combination of MMP-9 or its functionally equivalent fragment and active compounds may be applied in a subsequent manner or a simultaneous manner. In a preferred embodiment, the mixture will be in the form of an aqueous solution. In other embodiments, the mixture will be a powder or a dried, powdered, or lyophilized form of the mixture. In some embodiments, these forms will be re-hydrated before delivery.

In another embodiment of the present invention, a composition for enhancing intranasal delivery of active compounds includes MMP-9 or its functionally equivalent fragment both as the enhancing agent and as the active compounds. MMP-9 or its functionally equivalent fragment has its unique functionalities of modulating the tight junctions of the nasal epithelial cells, partially digesting the basal lamina and degrading type IV collagen, and possibly facilitating access to perineural, perivascular, or fila olfactoria compartment spaces, and therefore, it may be applied as an active compound to treat a related disease. In a preferred embodiment, the preparation will be in the form of an aqueous solution. In other embodiments, the mixture will be a powder or a dried or lyophilized form of the mixture, possibly re-hydrated before delivery.

The composition of the present invention may also include an apparatus designed for nasal delivery, such as a nebulizer or sprayer, that has been charged with the MMP-9 or its functionally equivalent fragment preparation. One suitable apparatus is a squeeze bottle used for antihistamine nasal sprays, including ASTELIN (azelastine hydrochloride; Medpointe Healthcare Inc.) and PATANASE (olopatadine hydrochloride; Alcon, Inc.). Suitable examples of delivery devices would include nasal pump sprays, such as the APTAR PHARMA nasal spray pump, controlled particle dispersion devices, such as VIANASE electronic atomizer, nasal aerosol devices, such as ZETONNA nasal aerosol, nasal nebulization devices, such as EASYNOSE nebulizer, powder nasal delivery devices, such as OPTINOSE breath-powered nasal delivery device, and atomized nasal medication devices, such as LMA MAD NASAL device.

In one aspect, the present invention relates to a composition comprising MMP-9 and other suitable agents for enhancing intranasal delivery of an active compound. The active compound may comprise MMP-9. Upon administration of the composition and/or the active compound, a suitable amount of the active compound may be delivered into the central nervous system. The suitable amount of the active compound such as antibodies or antibody fragments in the central nervous system of a patient has been previously discussed by Adolfsson, Pihlgren, et al. (Adolfsson, Pihlgren, et al. 2012). The suitable amount of the active compound in the central nervous system of a patient may be any amount of the active compound which causes the treatment of the disease condition of the patient. For example, the suitable amount of an antibody or an antibody fragment in the central nervous system of a patient may be about sub 100 pM. In one specific embodiment, the suitable amount of an antibody or an antibody fragment in the central nervous system of a patient may be in the range of about 10 pM to 100 pM.

Formulations of the Present Invention

In one aspect, the present invention relates to formulations for enhancing intranasal delivery of therapeutic agents. In one configuration, the present formulations may include MMP-9 or a functionally equivalent fragment both as the enhancing agent and the active compound. In this configuration, the present formulations may be free of any other active compounds.

In one embodiment, the present formulations may include MMP-9 or a functionally equivalent fragment and any other suitable agents.

Suitable Carrier Or Vehicle

Suitable agents may include a suitable carrier or vehicle for intranasal mucosal delivery. As used herein, the term "carrier" refers to a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, may be found in the *U.S. Pharmacopeia National Formulary*, 1857-1859, (1990).

Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other non toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator.

Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

Absorption-Promoting Agents

Suitable agents may include any suitable absorption-promoting agents. The suitable absorption-promoting agents may be selected from small hydrophilic molecules, including but not limited to, dimethyl sulfoxide (DMSO), dimethylformamide, ethanol, propylene glycol, and the 2-pyrrolidones. Alternatively, long-chain amphipathic molecules, for example, deacyl methyl sulfoxide, azone, sodium lauryl sulfate, oleic acid, and the bile salts, may be employed to enhance mucosal penetration of the MMP-9 or a functionally equivalent fragment. In additional aspects, surfactants (e.g., polysorbates) are employed as adjunct compounds, processing agents, or formulation additives to enhance intranasal delivery of the MMP-9 or a functionally equivalent fragment. Agents such as DMSO, polyethylene glycol, and ethanol can, if present in sufficiently high concentrations in delivery environment (e.g., by pre-administration or incorporation in a therapeutic formulation), enter the aqueous phase of the mucosa and alter its solubilizing properties, thereby enhancing the partitioning of the MMP-9 or a functionally equivalent fragment from the vehicle into the mucosa.

Delivery-Enhancing Agents

Suitable agents may include suitable delivery-enhancing agents. The suitable delivery-enhancing agents may include (A) solubilization agents; (B) charge modifying agents; (C) pH control agents; (D) degradative enzyme inhibitors; (E) mucolytic or mucus clearing agents; (F) ciliostatic agents; (G) membrane penetration-enhancing agents (e.g., (i) a surfactant, (ii) a bile salt, (iii) a phospholipid or fatty acid additive, mixed micelle, liposome, or carrier, (iv) an alcohol, (v) an enamine, (iv) an NO donor compound, (vii) a long-chain amphipathic molecule (viii) a small hydrophobic penetration enhancer; (ix) sodium or a salicylic acid derivative; (x) a glycerol ester of acetoacetic acid (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, (xviii) an inhibitor of cholesterol synthesis; or (xiv) any combination of the membrane penetration enhancing agents of (i)-(xviii)); (H) modulatory agents of epithelial junction physiology, such as nitric oxide (NO) stimulators, chitosan, and chitosan derivatives; (I) vasodilator or vasoconstrictor agents; (J) selective transport-enhancing agents; and (K) stabilizing delivery vehicles, carriers, supports or complex-forming species with which the MMP-9 or a functionally equivalent fragment is effectively combined, associated, contained, encapsulated or bound to stabilize the active agent for enhanced mucosal delivery. Suitable vasoconstrictor agents have been previously described by Dhuria, Hanson, et al. (Dhuria, Hanson, et al., 2009).

Additional intranasal mucosal delivery-enhancing agents that are useful within the coordinated administration and processing methods and combinatorial formulations of the invention may also include, but are not limited to, mixed micelles; enamines; nitric oxide donors (e.g., S-nitroso-N-acetyl-DL-penicillamine, NOR1, NOR4—which are preferably co-administered with an NO scavenger such as carboxy-PITO or diclofenac sodium); sodium salicylate; glycerol esters of acetoacetic acid (e.g., glyceryl-1,3-diacetoacetate or 1,2-isopropylideneglycerine-3-acetoacetate); and other release-diffusion or intra- or trans-epithelial penetration-promoting agents that are physiologically compatible for intranasal mucosal delivery. Other absorption-promoting agents may be selected from a variety of carriers, bases and excipients that enhance mucosal delivery, stability, activity or trans-epithelial penetration of the MMP-9 or a functionally equivalent fragment. These include, inter alia, cyclodextrins and β-cyclodextrin derivatives (e.g., 2-hydroxypropyl-β-cyclodextrin and heptakis(2,6-di-O-methyl-β-cyclodextrin). These compounds, optionally conjugated with one or more of the active ingredients and further optionally formulated in an oleaginous base, enhance bioavailability in the intranasal mucosal formulations of the invention. Yet additional absorption-enhancing agents adapted for intranasal mucosal delivery may also include medium-chain fatty acids, including mono- and diglycerides (e.g., sodium caprate—extracts of coconut oil, CAPMUL), and triglycerides (e.g., amylodextrin, Estaram 299, Miglyol 810).

Penetration-Promoting Agent

In another embodiment, the intranasal mucosal therapeutic and prophylactic formulations of the present invention may also be supplemented with any suitable penetration-promoting agent that facilitates absorption, diffusion, or penetration of MMP-9 or a functionally equivalent fragment across mucosal barriers. The penetration promoter may be any promoter that is pharmaceutically acceptable. Thus, in more detailed aspects of the invention formulations are provided that incorporate one or more penetration-promoting agents selected from sodium salicylate and salicylic acid derivatives (acetyl salicylate, choline salicylate, salicylamide, etc.); amino acids and salts thereof (e.g. monoaminocarboxlic acids such as glycine, alanine, phenylalanine, proline, hydroxyproline, etc.; hydroxyamino acids such as serine; acidic amino acids such as aspartic acid, glutamic acid, etc; and basic amino acids such as lysine etc—inclusive of their alkali metal or alkaline earth metal salts); and N-acetylamino acids (N-acetylalanine, N-acetylphenylalanine, N-acetylserine, N-acetylglycine, N-acetyllysine, N-acetylglutamic acid, N-acetylproline, N-acetylhydroxyproline, etc.) and their salts (alkali metal salts and alkaline earth metal salts).

Also provided as penetration-promoting agents within the methods and compositions of the invention are substances which are generally used as emulsifiers (e.g. sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidonecarboxylic acids, alkylpyrrolidones carboxylic acid esters, N-alkylpyrrolidones, proline acyl esters, and the like.

Within various aspects of the invention the intranasal delivery formulations and methods are provided that allow delivery of MMP-9 or its functionally equivalent fragment and/or other therapeutic agents across BBB barriers between administration and selected target sites. Certain formulations may be specifically adapted for a selected target cell, tissue or organ, or even a particular disease state. In other aspects, formulations and methods provide for efficient, selective endo- or transcytosis of MMP-9 or its functionally equivalent fragment specifically routed along a defined intracellular or intercellular pathway.

Typically, the MMP-9 or its functionally equivalent fragment and/or any active compounds may be efficiently loaded at effective concentration levels in a carrier or other delivery vehicle, and may be delivered and maintained in a stabilized form, e.g., at the nasal mucosa and/or during passage through intracellular compartments and membranes to a remote target site for drug action (e.g., the blood stream or a defined tissue, organ, or extracellular compartment). The MMP-9 or its functionally equivalent fragment may be provided in a delivery vehicle or otherwise modified (e.g., in the form of a prodrug), wherein release or activation of the MMP-9 or its functionally equivalent fragment may be triggered by a physiological stimulus (e.g. pH change, lysosomal enzymes, etc.).

In certain embodiments, MMP-9 or its functionally equivalent fragment may be pharmacologically inactive until it reaches its target site for activity. In most cases, the MMP-9 or its functionally equivalent fragment and other formulation components may be non-toxic and non-immunogenic. In this context, carriers and other formulation components may be generally selected for their ability to be rapidly degraded and excreted under physiological conditions. At the same time, formulations may be chemically and physically stable in dosage form for effective storage.

In another configuration, the present formulations may include MMP-9 or a functionally equivalent fragment as the enhancing agent and any other suitable active compounds. In this configuration, the present formulations may include MMP-9 or a functionally equivalent fragment as the enhancing agent for enhancing the delivery of any suitable active compounds. The present formulations may also include any suitable agents as discussed above. In one embodiment, the present formulations may include intranasal co-administering MMP-9 or a functionally equivalent fragment and any other suitable active compounds along with any suitable agents. In another embodiment, the present formulations may include initially intranasally administering MMP-9 or a functionally equivalent fragment and subsequently intranasally administering any suitable active compounds.

Stabilization Agent

In another configuration, the present formulation may also comprise other suitable agents that stabilize the formulations. For example, an approach for stabilizing solid protein formulations of the invention is to increase the physical stability of purified, e.g., lyophilized, protein. This will inhibit aggregation via hydrophobic interactions as well as via covalent pathways that may increase as proteins unfold. Stabilizing formulations in this context may often include polymer-based formulations, for example a biodegradable hydrogel formulation/delivery system. The critical role of water in protein structure, function, and stability is well known. Typically, proteins are relatively stable in the solid state with bulk water removed. However, solid therapeutic protein formulations may become hydrated upon storage at elevated humidities or during delivery from a sustained release composition or device. The stability of proteins generally drops with increasing hydration. Water may also play a significant role in solid protein aggregation, for example, by increasing protein flexibility resulting in enhanced accessibility of reactive groups, by providing a mobile phase for reactants, and by serving as a reactant in several deleterious processes such as beta-elimination and hydrolysis.

An effective method for stabilizing peptides and proteins against solid-state aggregation for mucosal delivery may be to control the water content in a solid formulation and maintain the water activity in the formulation at optimal levels. This level depends on the nature of the protein, but in general, proteins maintained below their "monolayer" water coverage will exhibit superior solid-state stability.

A variety of additives, diluents, bases and delivery vehicles may be provided within the invention that effectively control water content to enhance protein stability. These reagents and carrier materials effective as anti-aggregation agents in this sense may include, for example, polymers of various functionalities, such as polyethylene glycol, dextran, diethylaminoethyl dextran, and carboxymethyl cellulose, which significantly increase the stability and reduce the solid-phase aggregation of peptides and proteins admixed therewith or linked thereto. In some instances, the activity or physical stability of proteins may also be enhanced by various additives to aqueous solutions of the peptide or protein drugs. For example, additives, such as polyols (including sugars), amino acids, proteins such as collagen and gelatin, and various salts may be used.

Certain additives, in particular sugars and other polyols, may also impart significant physical stability to dry, e.g., lyophilized proteins. These additives may also be used within the invention to protect the proteins against aggregation not only during lyophilization but also during storage in the dry state. For example sucrose and Ficoll 70 (a polymer with sucrose units) exhibit significant protection against peptide or protein aggregation during solid-phase incubation under various conditions. These additives may also enhance the stability of solid proteins embedded within polymer matrices.

Yet additional additives, for example sucrose, stabilize proteins against solid-state aggregation in humid atmospheres at elevated temperatures, as may occur in certain sustained-release formulations of the invention. Proteins such as gelatin and collagen also serve as stabilizing or bulking agents to reduce denaturation and aggregation of unstable proteins in this context. These additives can be incorporated into polymeric melt processes and compositions within the invention. For example, polypeptide microparticles can be prepared by simply lyophilizing or spray drying a solution containing various stabilizing additives described above. Sustained release of unaggregated peptides and proteins can thereby be obtained over an extended period of time.

Various additional preparative components and methods, as well as specific formulation additives, are provided herein which yield formulations for mucosal delivery of aggregation-prone peptides and proteins, wherein the peptide or protein is stabilized in a substantially pure, unaggregated form using a solubilization agent. A range of components and additives are contemplated for use within these methods and formulations. Exemplary of these solubilization agents are cyclodextrins (CDs), which selectively bind hydrophobic side chains of polypeptides. These CDs have been found to bind to hydrophobic patches of proteins in a manner that significantly inhibits aggregation. This inhibition is selective with respect to both the CD and the protein involved. Such selective inhibition of protein aggregation may provide additional advantages within the intranasal delivery methods and compositions of the invention.

Additional agents for use in this context include CD dimers, trimers and tetramers with varying geometries controlled by the linkers that specifically block aggregation of peptides and protein. Yet solubilization agents and methods for incorporation within the invention involve the use of peptides and peptide mimetics to selectively block protein-protein interactions. In one aspect, the specific binding of hydrophobic side chains reported for CD multimers may be extended to proteins via the use of peptides and peptide mimetics that similarly block protein aggregation. A wide range of suitable methods and anti-aggregation agents may be available for incorporation within the compositions and procedures of the invention.

Degradative Enzyme Inhibitory Agent

In another embodiment, the present formulation may also comprise other suitable agents such as a degradative enzyme inhibitory agent. As used herein, the term "degradative enzyme inhibitory agent" refers to any inhibitor that inhibits the activity of an enzyme to protect the biologically active agent(s) may be usefully employed in the compositions and methods of the invention. Exemplary mucoadhesive polymer-enzyme inhibitor complexes that are useful within the mucosal delivery formulations and methods of the invention include, but are not limited to: Carboxymethylcellulose-pepstatin (with anti-pepsin activity); Poly(acrylic acid)-Bowman-Birk inhibitor (anti-chymotrypsin); Poly(acrylic acid)-chymostatin (anti-chymotrypsin); Poly(acrylic acid)-elastatinal (anti-elastase); Carboxymethylcellulose-elastatinal (anti-elastase); Polycarbophil—elastatinal (anti-elastase); Chitosan—antipain (anti-trypsin); Poly(acrylic acid—bacitracin (anti-aminopeptidase N); Chitosan—EDTA (anti-aminopeptidase N, anti-carboxypeptidase A); Chitosan—EDTA—antipain (anti-trypsin, anti-chymotrypsin, anti-elastase). As described in further detail below, certain embodiments of the invention will optionally incorporate a novel chitosan derivative or chemically modified form of chitosan. One such novel derivative for use within the invention is denoted as a $\beta$-$[1{\rightarrow}4]$-2-guanidino-2-deoxy-D-glucose polymer (poly-GuD).

Mucolytic and Mucus-Clearing Agents

In another embodiment, the present formulation may also comprise other suitable agents such as mucolytic and mucus-clearing agents. The term "mucolytic and mucus-clearing agents", as used herein, refers to any agents which may serve to degrade, thin or clear mucus from intranasal mucosal surfaces to facilitate absorption of intranasally administered biotherapeutic agents. A variety of mucolytic or mucus-clearing agents are available for incorporation within the methods and compositions of the invention. Based on their mechanisms of action, mucolytic and mucus clearing agents can often be classified into the following groups: proteases (e.g., pronase, papain) that cleave the protein core of mucin glycoproteins; sulfhydryl compounds that split mucoprotein disulfide linkages; and detergents (e.g., Triton X-100, Tween 20) that break non-covalent bonds within the mucus. Additional compounds in this context include, but are not limited to, bile salts and surfactants, for example, sodium deoxycholate, sodium taurodeoxycholate, sodium glycocholate, and lysophosphatidylcholine.

The effectiveness of bile salts in causing structural breakdown of mucus is in the order deoxycholate>taurocholate>glycocholate. Other effective agents that reduce mucus viscosity or adhesion to enhance intranasal delivery according to the methods of the invention include, e.g., short-chain fatty acids, and mucolytic agents that work by chelation, such as N-acylcollagen peptides, bile acids, and saponins (the latter function in part by chelating $Ca^{2+}$ and/or $Mg^{2+}$ which play an important role in maintaining mucus layer structure).

Ciliostatic Agents

In another embodiment, the present formulation may also comprise other suitable agents such as ciliostatic agents. As used herein, the term "ciliostatic agents" refers to any agents which are capable of moving a layer of mucus along the mucosa to removing inhaled particles and microorganisms. For use within these aspects of the invention, the foregoing ciliostatic factors, either specific or indirect in their activity, are all candidates for successful employment as ciliostatic agents in appropriate amounts (depending on concentration, duration and mode of delivery) such that they yield a transient (i.e., reversible) reduction or cessation of mucociliary clearance at a mucosal site of administration to enhance delivery of MMP-9 or a functionally equivalent fragment, and other biologically active agents disclosed herein, without unacceptable adverse side effects.

Within more detailed aspects, a specific ciliostatic factor may be employed in a combined formulation or coordinate administration protocol with MMP-9 or its functionally equivalent fragment, and/or other biologically active agents disclosed herein. Various bacterial ciliostatic factors isolated and characterized in the literature may be employed within these embodiments of the invention. Ciliostatic factors from the bacterium *Pseudomonas aeruginosa* include a phenazine derivative, a pyo compound (2-alkyl-4-hydroxyquinolines), and a rhamnolipid (also known as a hemolysin). The pyo compound produced ciliostasis at concentrations of 50 μg/ml and without obvious ultrastructural lesions. The phenazine derivative also inhibited ciliary motility but caused some membrane disruption, although at substantially greater concentrations of 400 μg/ml. Limited exposure of tracheal explants to the rhamnolipid resulted in ciliostasis, which is associated with altered ciliary membranes. More extensive exposure to rhamnolipid is associated with removal of dynein arms from axonemes.

Vasodilator Agents

In another embodiment, the present formulation may also comprise other suitable agents such as vasodilator agents. As used herein, the term "vasodilator agents" refers to any agents which are vasoactive. A vasodilator agent may function within the invention to modulate the structure and physiology of the submucosal vasculature, increasing the transport rate of MMP-9 or its functionally equivalent fragment, and other biologically active agents into or through the mucosal epithelium and/or to specific target tissues or compartments (e.g., the systemic circulation or central nervous system.). Vasodilator agents for use within the invention typically cause submucosal blood vessel relaxation by either a decrease in cytoplasmic calcium, an increase in nitric oxide (NO) or by inhibiting myosin light chain kinase. They are generally divided into 9 classes: calcium antagonists, potassium channel openers, ACE inhibitors, angiotensin-II receptor antagonists, α-adrenergic and imidazole receptor antagonists, β1-adrenergic agonists, phosphodiesterase inhibitors, eicosanoids and NO donors. Within certain methods and compositions of the invention, a selected vasodilator agent may be coordinately administered (e.g., systemically or intranasally, simultaneously or in combinatorially effective temporal association) or combinatorially formulated with one or more MMP-9 or a functionally equivalent fragment, and other biologically active agent(s) in an amount effective to enhance the mucosal absorption of the active agent(s) to reach a target tissue or compartment in the subject (e.g., the liver, hepatic portal vein, CNS tissue or fluid, or blood plasma).

Vasoconstrictor Agents

In another embodiment, the present formulation may also comprise other suitable agents such as vasoconstrictor agents. As used herein, the term "vasoconstrictor agents" refers to any substances which may cause vasoconstriction. Vasoconstrictor agents may also be called vasoconstrictors, vasopressors, or simply "pressors". Vasoconstrictor agents may usually cause an increase in systemic blood pressure, but when they are administered in specific tissues, localized blood flow may be reduced. The extent of vasoconstriction may be slight or severe depending on the substance of vasoconstrictor agents or circumstance. Many vasoconstrictor agents may also cause pupil dilation. Vasoconstrictor agents may include any suitable substances such as antihistamines, decongestants and stimulants that are used to treat ADHD. Suitable vasoconstrictor agents have been previously described by Dhuria, Hanson, et al. (Dhuria, Hanson, et al., 2009).

Nitric Oxide Donor Agents

In another embodiment, the present formulation may also comprise other suitable agents such as nitric oxide donor agents. As used herein, the term "nitric oxide donor agents" refers to any suitable agents which are capable of releasing nitric oxide. A nitric oxide (NO) donor may be selected as a membrane penetration-enhancing agent to enhance mucosal delivery of MMP-9 or a functionally equivalent fragment, and other biologically active agents disclosed herein. Various NO donors are known in the art and are useful in effective concentrations within the methods and formulations of the invention. Exemplary NO donors include, but are not limited to, nitroglycerine, nitroprusside, NOC5 [3-(2-hydroxy-1-(methyl-ethyl)-2-nitrosohydrazino)-1-propanamine], NOC12 [N-ethyl-2-(1-ethyl-hydroxy-2-nitrosohydrazino)-ethanamine], SNAP [S-nitroso-N-acetyl-DL-penicillamine], NORI and NOR4. Within the methods and compositions of the invention, an effective amount of a selected NO donor may be coordinately administered or combinatorially formulated with MMP-9 or a functionally equivalent fragment, and/or other biologically active agents disclosed herein, into or through the mucosal epithelium.

Selective Transport-Enhancing Agents

In another embodiment, the present formulation may also comprise other suitable agents such as selective transport-enhancing agents. As used herein, the term "selective transport-enhancing agent" refers to any agent that facilitates transport of MMP-9 or a functionally equivalent fragment and/or one or more biologically active agents. The compositions and delivery methods of the invention may optionally incorporate a selective transport-enhancing agent that facilitates transport of one or more biologically active agents. These transport-enhancing agents may be employed in a combinatorial formulation or coordinate administration protocol with MMP-9 or a functionally equivalent fragment disclosed herein, to coordinately enhance delivery of one or more additional biologically active agent(s) across mucosal transport barriers, to enhance mucosal delivery of the active agent(s) to reach a target tissue or compartment in the subject (e.g., the mucosal epithelium, CNS tissue or fluid, or blood plasma). Alternatively, the transport-enhancing agents may be employed in a combinatorial formulation or coordinate administration protocol to directly enhance mucosal delivery of MMP-9 or a functionally equivalent fragment, with or without enhanced delivery of an additional biologically active agent.

Exemplary selective transport-enhancing agents for use within this aspect of the invention may include, but are not limited to, glycosides, sugar-containing molecules, and binding agents such as lectin binding agents, which are known to interact specifically with epithelial transport barrier components. For example, specific "bioadhesive" ligands, including various plant and bacterial lectins, which bind to cell surface sugar moieties by receptor-mediated interactions can be employed as carriers or conjugated transport mediators for enhancing mucosal, e.g., nasal delivery of biologically active agents within the invention. Certain bioadhesive ligands for use within the invention will mediate transmission of biological signals to epithelial target cells that trigger selective uptake of the adhesive ligand by specialized cellular transport processes (endocytosis or transcytosis). These transport mediators can therefore be employed as a "carrier system" to stimulate or direct selective uptake of one or more MMP-9 or functionally equivalent fragment proteins, analogs and mimetics, and other biologically active agent(s) into and/or through mucosal epithelia. These and other selective transport-enhancing agents significantly enhance mucosal delivery of macromolecular biopharmaceuticals (particularly peptides, proteins, oligonucleotides and polynucleotide vectors) within the invention.

Stabilizing Delivery Vehicle, Carrier, Support or Complex-Forming Species

In another embodiment, the present formulation may also comprise other suitable agents such as a stabilizing delivery vehicle, carrier, support or complex-forming species. The coordinate administration methods and combinatorial formulations of the instant invention may optionally incorporate effective lipid or fatty acid based carriers, processing agents, or delivery vehicles, to provide improved formulations for mucosal delivery of MMP-9 or functionally equivalent fragment proteins, analogs and mimetics, and other biologically active agents. For example, a variety of formulations and methods are provided for mucosal delivery which comprise one or more of these active agents, such as a peptide or protein, admixed or encapsulated by, or coordinately administered with, a liposome, mixed micellar carrier, or emulsion, to enhance chemical and physical stability and increase the half-life of the biologically active agents (e.g., by reducing susceptibility to proteolysis, chemical modification and/or denaturation) upon mucosal delivery.

Within certain aspects of the invention, specialized delivery systems for biologically active agents may comprise small lipid vesicles known as liposomes or micelles. These are typically made from natural, biodegradable, non-toxic, and non-immunogenic lipid molecules, and can efficiently entrap or bind drug molecules, including peptides and proteins, into, or onto, their membranes. The attractiveness of liposomes as a peptide and protein delivery system within the invention is increased by the fact that the encapsulated proteins can remain in their preferred aqueous environment within the vesicles, while the liposomal membrane protects them against proteolysis and other destabilizing factors. Even though not all liposome preparation methods known are feasible in the encapsulation of peptides and proteins due to their unique physical and chemical properties, several methods allow the encapsulation of these macromolecules without substantial deactivation.

Additional delivery vehicles carrier, support or complex-forming species for use within the invention may include long and medium chain fatty acids, as well as surfactant mixed micelles with fatty acids. Most naturally occurring lipids in the form of esters have important implications with regard to their own transport across mucosal surfaces. Free fatty acids and their monoglycerides which have polar groups attached have been demonstrated in the form of mixed micelles to act on the intestinal barrier as penetration enhancers. This discovery of barrier modifying function of free fatty acids (carboxylic acids with a chain length varying from 12 to 20 carbon atoms) and their polar derivatives has stimulated extensive research on the application of these agents as mucosal absorption enhancers.

For use within the methods of the invention, long chain fatty acids, especially fusogenic lipids (unsaturated fatty acids and monoglycerides such as oleic acid, linoleic acid, linoleic acid, monoolein, etc.) provide useful carriers to enhance mucosal delivery of MMP-9 or a functionally equivalent fragment, and other biologically active agents disclosed herein. Medium chain fatty acids (C6 to C12) and monoglycerides have also been shown to have enhancing activity in intestinal drug absorption and can be adapted for use within the mucosal delivery formulations and methods of the invention. In addition, sodium salts of medium and long chain fatty acids are effective delivery vehicles and absorption-enhancing agents for mucosal delivery of biologically active agents within the invention. Thus, fatty acids can be employed in soluble forms of sodium salts or by the addition of non-toxic surfactants, e.g., polyoxyethylated hydrogenated castor oil, sodium taurocholate, etc. Other fatty acid and mixed micellar preparations that are useful within the invention include, but are not limited to, Na caprylate (C8), Na caprate (C10), Na laurate (C12) or Na oleate (C18), optionally combined with bile salts, such as glycocholate and taurocholate.

Devices and Kits of the Present Invention

In another aspect, the present invention relates to a therapeutic device for intranasal delivery. In one embodiment, the therapeutic device may comprise any suitable devices charged with a preparation of MMP-9 or a functionally equivalent fragment. In another embodiment, the therapeutic device may comprise any suitable devices charged with a preparation of MMP-9 or a functionally equivalent fragment and at least one additional active compound.

The instant invention may also include kits, packages and multicontainer units containing the above described pharmaceutical compositions, active ingredients, and/or means for administering the same for use in the prevention and treatment of diseases and other conditions in mammalian subjects. Briefly, these kits include a container or formulation that contains MMP-9 or a functionally equivalent fragment, and/or other biologically active agents in combination with mucosal delivery enhancing agents disclosed herein formulated in a pharmaceutical preparation for mucosal delivery.

The intranasal formulations of the present invention can be administered using any spray bottle or syringe, or by instillation. An example of a nasal spray bottle is the, "Nasal Spray Pump w/Safety Clip, Pfeiffer SAP #60548, which delivers a dose of 0.1 mL per squirt and has a diptube length of 36.05 mm. It can be purchased from Pfeiffer of America of Princeton, N.J.

In one embodiment, the intranasal formulations of the present invention may be administered using a nasal spray or aerosol. Any kits or devices capable of producing a nasal spray or aerosol may be used for the present invention. Specifically, a suitable kit or device may be any form of the following spray or aerosol:
1. Aerosol—A product that is packaged under pressure and contains therapeutically active ingredients that are released upon activation of an appropriate valve system.
2. Metered aerosol—A pressurized dosage form comprised of metered dose valves, which allow for the delivery of a uniform quantity of spray upon each activation.
3. Powder aerosol—A product that is packaged under pressure and contains therapeutically active ingredients in the form of a powder, which are released upon activation of an appropriate valve system.
4. Spray aerosol—An aerosol product that utilizes a compressed gas as the propellant to provide the force necessary to expel the product as a wet spray; it generally applicable to solutions of medicinal agents in aqueous solvents.
5. Spray—A liquid minutely divided as by a jet of air or steam. Nasal spray drug products contain therapeutically active ingredients dissolved or suspended in solutions or mixtures of excipients in non-pressurized dispensers.
6. Metered spray—A non-pressurized dosage form consisting of valves that allow the dispensing of a specified quantity of spray upon each activation.
7. Suspension spray—A liquid preparation containing solid particles dispersed in a liquid vehicle and in the form of course droplets or as finely divided solids.

In one specific embodiment, a suitable kit or device may comprise a metered nasal spray pump.

In another embodiment, the intranasal formulations of the present invention may be administered by a transport system. Any suitable transport system may be used for the present invention. For example, in a liquid form, the intranasal formulations of the present invention may be transported by a suitable liquid transport system to mucosal surfaces for intranasal delivery. A suitable liquid transport system may include a swab. Another suitable transport system may include PURITAN liquid Amies transport system.

EXAMPLES

Example 1

Intranasal Administration of MMP-9 or its Functionally Equivalent Fragment and Active Compounds. In the present example, MMP-9 or its functionally equivalent fragment and active compounds in their respective effective amount are intranasally applied to the patients such as rats in a subsequent or a simultaneous manner. MMP-9 or its functionally equivalent fragment is initially prepared as an aqueous solution having a concentration of 100 nanomolar (nM). Female Sprague Dawley rats (180-220 g) were anesthetized with urethane (1.5 g/kg i.p.). Either saline or a MMP-9 or its functionally equivalent fragment solution (100 nM) was intranasally (IN) administered to alternating nares in 6 µL drops every 5 minutes (total volume=24 µL). This was followed by intranasal administration of 3 kDa lysine-fixable Texas Red dextran (Dex3, Invitrogen; 50 g/L) or 10 kDa lysine-fixable Texas Red dextran (Dex10, Invitrogen; 50 g/L) to alternating nares in 6 µL drops every 5 minutes (total volume=24 µL).

As a control experiment, some rats received an intra-arterial (IA) injection of 10 dex (0.2 µg in 500 µL saline) following intranasal administration of MMP-9 or its functionally equivalent fragment. 30 min after Dex10 administration, rats were perfused with 50 mL phosphate buffered saline followed by 500 mL 4% paraformaldehyde and the whole brain or 1 mm sagittal sections were viewed under an Olympus MVX10 fluorescent macro zoom microscope equipped with a Texas Red filter set. Images were acquired with an Orca-flash 2.8 CMOS camera (Hamamatsu) at the same magnification under the same light intensity and exposure time for each treatment group. Plasma samples were collected from the abdominal aorta and the concentration of Dex10 was determined on a fluorescent plate reader (BMG Labtech) with the excitation and emission filters set at 584 nm and 620 nm respectively.

Figure 6:
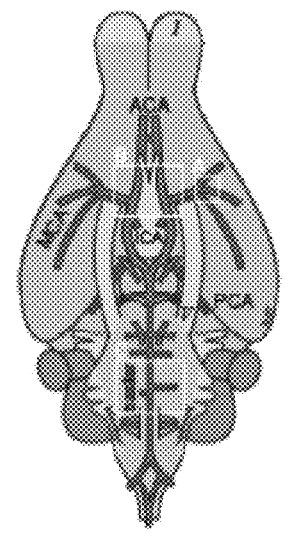
FIG. 6 is a set of perivascular fluorescence images following intranasal (IN) applications of saline (left) or Texas Red-labeled 3 kDa dextran (Dex3) (right).

Referring now to FIG. 6, perivascular fluorescence images are depicted following intranasal (IN) applications of saline (left) or Texas Red-labeled 3 kDa dextran (Dex3) (right) Compared with the image resulting from a controlled experiment (FIG. 1; left), the existence of Dex3 shown as red color in the perivascular spaces of the middle cerebral artery (MCA) indicates that Dex3 has been intranasally delivered into the CNS. As shown below, a larger dextran, such as 10 kDa lysine-fixable Texas Red dextran, not capable of self transport into the CNS, essentially requires MMP-9 as an enhancer.

Alternatively, MMP-9 or its functionally equivalent fragment and active compounds may be applied intranasally in a simultaneous manner. In the present example, MMP-9 or its functionally equivalent fragment is initially prepared as an aqueous solution having a concentration of 400 nanomolar (nM). Other concentrations of MMP-9 or its functionally equivalent fragment solutions may also be prepared. The MMP-9 or its functionally equivalent fragment solution is then mixed with active compounds such as Dex10 into a mixture solution.

The mixture solution of MMP-9 or its functionally equivalent fragment and Dex10 was intranasally (IN) administered to alternating nares in 6 μL drops every 5 minutes (total volume=24 μL). To show the effectiveness of MMP-9 or its functionally equivalent fragment, a saline solution is used as a controlled experiment. 30 min after Dex10 administration, rats were perfused with 50 mL phosphate buffered saline followed by 500 mL 4% paraformaldehyde and the whole brain or 1 mm sagittal sections were viewed under an Olympus MVX10 fluorescent macro zoom microscope equipped with a Texas Red filter set. Images were acquired with an Orca-flash 2.8 CMOS camera (Hamamatsu) at the same magnification under the same light intensity and exposure time for each treatment group. Plasma samples were collected from the abdominal aorta and the concentration of Dex10 was determined on a fluorescent plate reader (BMG Labtech) with the excitation and emission filters set at 584 nm and 620 nm respectively.

Intranasal application of 400 nM MMP-9 or its functionally equivalent fragment and Dex10 in a simultaneous manner appears to increase the delivery of Dex10 over the controlled experiment of saline, which however is not to extent of the delivery results observed during intranasal delivery of 100 nM MMP-9 or its functionally equivalent fragment and Dex10 in a subsequent manner. Though 3 kDa and 10 kDa lysine-fixable Texas Red dextran are used as examples for demonstration, a similar effect of intranasal delivery is expected for any therapeutic agents or active compounds, as is known to those skilled in the art.

Figure 7:
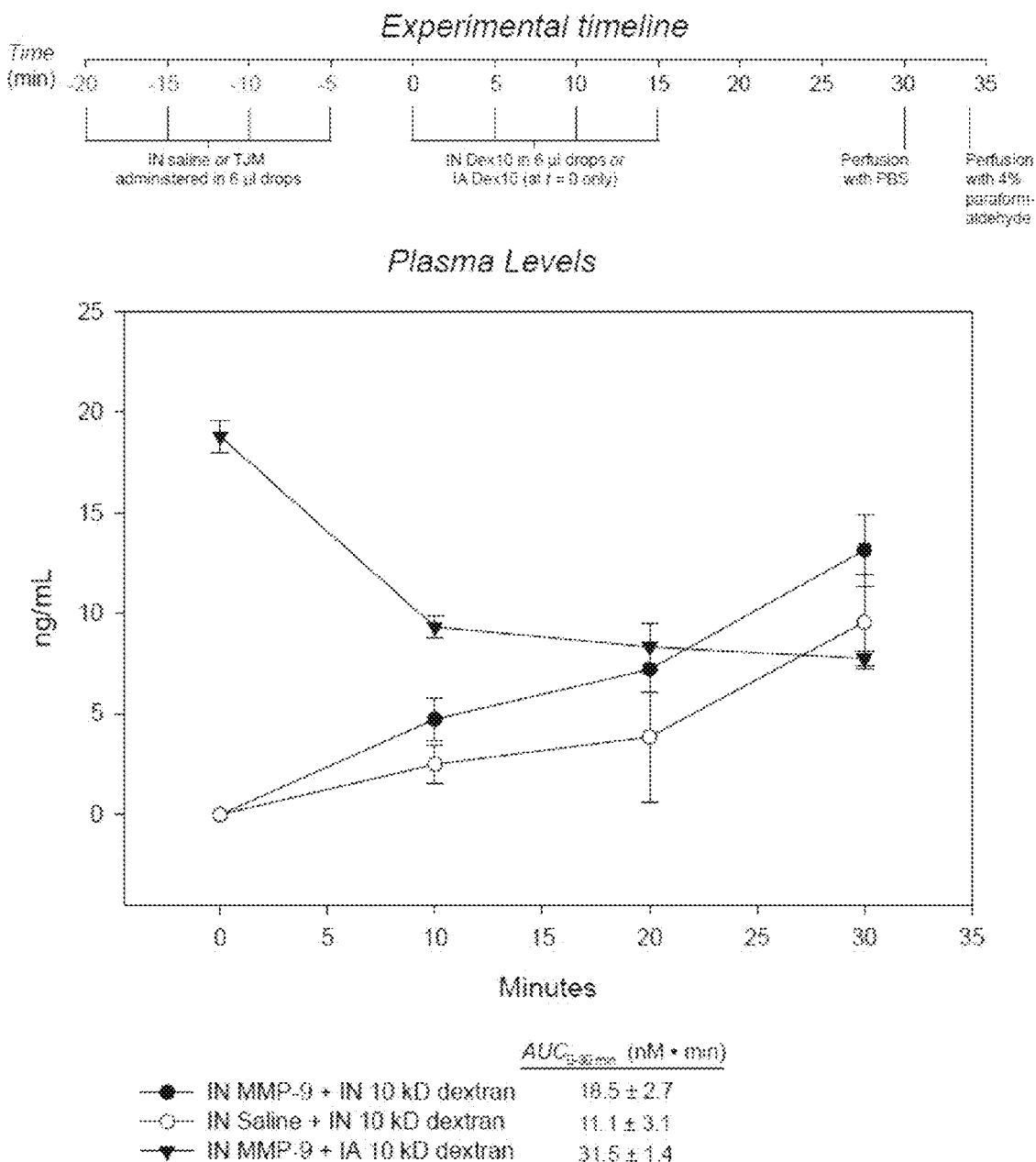
FIG. 7 is a diagram of timeline and plasma data following intranasal (IN) application of Texas Red-labeled 10 kDa dextran (Dex10) after intranasal (IN) or intra-arterial (IA) applications of saline or matrix metalloproteinase-9 (MMP-9; 100 nM).

As shown in FIG. 7, to further differentiate an intranasal (IN) delivery and an intra-arterial (IA) delivery, timeline and plasma data are depicted following intranasal (IN) or intra-arterial (IA) applications of Texas Red-labeled 10 kDa dextran (Dex10) after intranasal (IN) applications of saline or MMP-9 or its functionally equivalent fragment (100 nM). Plasma concentration observed following intra-arterial injection of Dex10 shortly after intranasal application of MMP-9 or its functionally equivalent fragment (green) appears to continuously decrease within 30 minutes, indicating that intra-arterial pathway does not contribute to the delivery from nasal systems to the CNS. Further, while plasma concentrations following intranasal application of Dex10 shortly after intranasal applications of both MMP-9 or its functionally equivalent fragment (red) and saline (blue) are increasing continuously in 30 minutes, that observed after intranasal application of MMP-9 or its functionally equivalent fragment shows a much faster rate of increase. Thus, these observations demonstrate that intranasal pre-treatment of MMP-9 or its functionally equivalent fragment is indeed enhancing the intranasal delivery of Dex10 from nasal system to the CNS.

Referring now to FIG. 8, widespread cerebral perivascular fluorescence images are depicted following intranasal (IN) application of Texas Red-labeled 10 kDa dextran (Dex10) after intranasal (IN) or intra-arterial (IA) applications of saline or MMP-9 or its functionally equivalent fragment (100 nM) monitored at the locations of circle of Willis (Location B) and basilar artery (Location C). Observations both on ventral brain surface (top) and on 1 mm sagittal section (bottom) show similar results. At both locations of circle of Willis (location B) and basilar artery (location C), similar observations have been made. For example, images observed following intranasal applications of MMP-9 or its functionally equivalent fragment and Dex10 in a subsequent manner (center) show a positive fluorescence detection of cerebral perivascular spaces, indicating consistent distribution of Dex10 throughout the CNS within perivascular spaces of the cerebral vasculature. The negative detections of fluorescence following both intranasal applications of saline and Dex10 in a subsequent manner (left) and intranasal application of MMP-9 or its functionally equivalent fragment and intra-arterial injection of Dex10 in a subsequent manner (right) suggest that intranasal pre-treatment of MMP-9 or its functionally equivalent fragment may facilitate intranasal delivery of Dex10 from nasal system to the widespread regions of the CNS.

Figure 9:
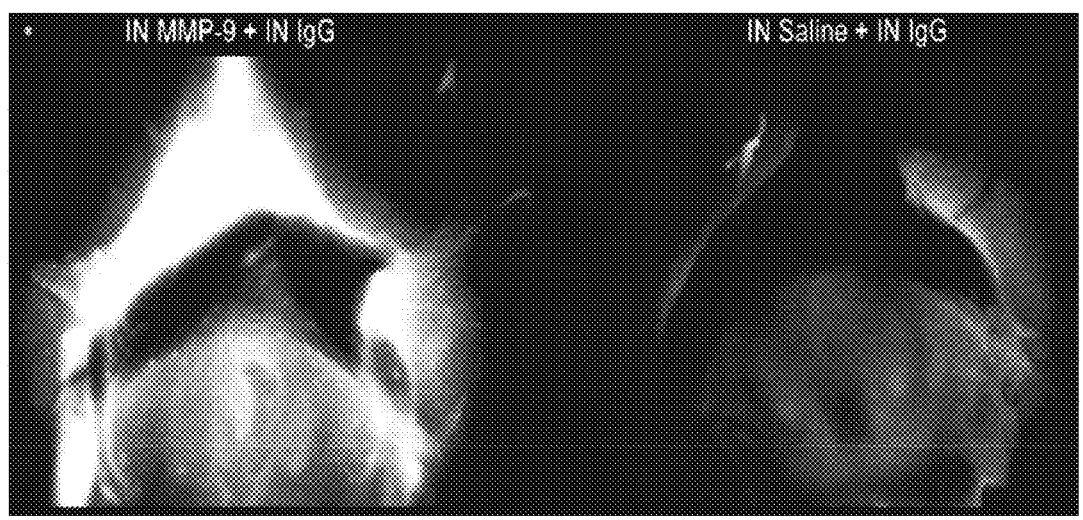
FIG. 9 is a set of widespread cerebral perivascular fluorescence images following intranasal (IN) applications of immunoglobulin G (IgG) after intranasal (IN) applications of matrix metalloproteinase-9 (MMP-9; 100 nM; left) or saline (right).

In order to further confirm the functionality of MMP-9 or its functionally equivalent fragment for enhancing intranasal delivery of various active compounds, Immunoglobulin G (IgG) has been used as another example of active compounds. In the present experiment, MMP-9 or its functionally equivalent fragment and IgG are applied intranasally in a subsequent manner. MMP-9 or its functionally equivalent fragment (100 nM) or saline are administrated to rats 20 minutes before intranasal administration of Alexafluor 568 labeled Immunoglobulin (IgG). After 30 minutes, the rats are perfused, and the brains are rapidly removed, and the circle of Willis on the ventral surface of the brain is imaged. Referring now to FIG. 9, widespread cerebral perivascular fluorescence images are depicted following intranasal (IN) applications of immunoglobulin G (IgG) after intranasal (IN) applications of MMP-9 or its functionally equivalent fragment (100 nM; left) or saline (right). The image observed following intranasal applications of MMP-9 or its functionally equivalent fragment and Dex10 in a subsequent manner (left) show a positive fluorescence detection of cerebral perivascular spaces, indicating consistent distribution of IgG throughout the CNS within perivascular spaces of the cerebral vasculature.

Example 2

Figure 10:
FIG. 10 is a set of widespread cerebral perivascular fluorescence images following intranasal (IN) applications (left and center) or intra-arterial (IA) applications (right) of Texas Red-labeled 10 kDa dextran (Dex10) after intranasal (IN) applications of matrix metalloproteinase-9 (MMP-9; 100 nM; left and right) or matrix metalloproteinase-2 (MMP-2; 300 nM; center).

Intranasal Administration of MMP-2 and Active Compounds. As another member of matrix metalloproteinases (MMP) family, matrix metalloproteinase-2 (MMP-2; gelatinase A) shows some similarity in structure to that of MMP-9 or its functionally equivalent fragment. Therefore, the functionalities of MMP-2 with MMP-9 or its functionally equivalent fragment are compared for enhancing intranasal delivery of active compounds. Referring now to FIG. 10, widespread cerebral perivascular fluorescence images are depicted following intranasal (IN) applications (left and center) or intra-arterial (IA) applications (right) of Texas Red-labeled 10 kDa dextran (Dex10) after intranasal (IN) applications of MMP-9 or its functionally equivalent fragment (100 nM; left and right) or matrix metalloproteinase-2 (MMP-2; 300 nM; center). Images observed following intranasal applications of MMP-2 (300 nM) and Dex10 in a subsequent manner (center) fail to detect fluorescence spectra of Dex10, indicating that unlike MMP-9 or its functionally equivalent fragment, intranasal pre-treatment of MMP-2 does not enhance the intranasal delivery of Dex10 under the condition of the present experiment. The different functionalities between MMP-2 and MMP-9 or its functionally equivalent fragment are likely due to their structural difference. In terms of amino acid sequences, MMP-2 and MMP-9 in rats appear to be 42.6% homologous, and MMP-2 and MMP-9 in human appear to be 43.3% homologous.

Example 3

Intranasal Co-Administration of MMP-9 And Active Compounds. Fluorescently labeled 10 kDa dextran (dex10) was used as an example of active compounds. The present invention may be applied to any other suitable active compounds. Intranasal co-administration of MMP-9 and fluorescently labeled 10 kDa dextran (dex10) results in widespread perivascular distribution in the brain. As shown in FIG. 11, rats were initially anesthetized with urethane and administered 12 µl drops of dex10 (25 mg/ml) in alternating nares every 5 minutes (48 µL total) with (A) or without (B) MMP-9 (100 nM). After 30 minutes following the first drop, rats were perfused with phosphate buffered saline followed by 4% paraformaldehyde. The brain was removed and 1 mm thick sections were viewed under an Olympus MVX10 fluorescent macro zoom microscope equipped with a Texas Red filter set. Images from the brainstem were acquired with an Orca-flash 2.8 CMOS camera (Hamamatsu) at the same magnification under the same light intensity and exposure time for each treatment group. Scale bar=100 µm. The image A shows that intranasal co-administration of MMP-9 and fluorescently labeled 10 kDa dextran (dex10) results in widespread perivascular distribution of dex10 in the brain. In the absence of MMP-9, no dex10 was present in the brain. Therefore, co-administration of MMP-9 and dex10 were assisting intranasal delivery of dex10 into the rat brain.

Example 4

Figure 12:
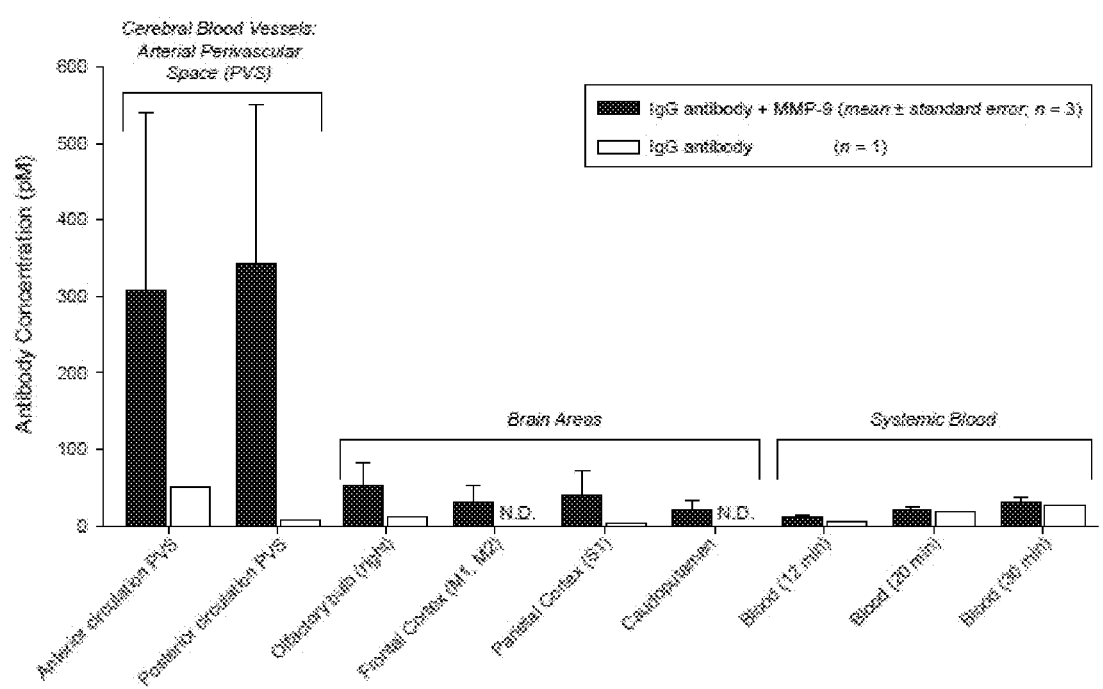
FIG. 12 is a graph showing tissue/fluid levels after Intranasal administration of $^{125}$I-labeled non-targeted rat IgG (~60 µg) to rats with or without MMP-9 pretreatment. Systemic arterial blood and microdissected samples of cerebral blood vessels and brain areas were assayed by gamma counting. Application of MMP-9 resulted in radiolabeled antibody concentrations that were approximately 6- to 50-fold higher in the cerebral blood vessel PVS, 4-fold higher in the olfactory bulb and at least 12-fold higher in the other brain areas indicated. Systemic blood levels were similar regardless of whether MMP-9 was applied or not. The specific activity of intranasally applied solutions were also similar between the two groups (IgG+MMP-9, 68.8±5.6 µCi administered; IgG only, 62.3 µCi administered). N.D., not detectable.

MMP-9 Pretreatment Leads to Higher Antibody Levels in the Brain Following Intranasal Administration. IgG was used as an example of antibodies or antibody fragments. Any other antibodies or antibody fragments may be suitable for the present invention. FIG. 12 is a graph showing Intranasal administration of $^{125}$I-labeled non-targeted rat IgG (~60 µg) to rats with or without MMP-9 pretreatment. Systemic arterial blood and microdissected samples of cerebral blood vessels and brain areas were assayed by gamma counting. As shown in FIG. 12, application of MMP-9 resulted in radiolabeled antibody concentrations that were approximately 6- to 50-fold higher in the cerebral blood vessel PVS, 4-fold higher in the olfactory bulb and at least 12-fold higher in the other brain areas indicated. Systemic blood levels were similar regardless of whether MMP-9 was applied or not. The specific activity of intranasally applied solutions were also similar between the two groups (IgG+MMP-9, 68.8±5.6 µCi administered; IgG only, 62.3 µCi administered). The observations show that MMP-9 pretreatment enhanced intranasal delivery of IgG to central nervous system areas.

FIG. 13 is a set of sagittal autoradiographs images showing $^{125}$I-labeled IgG antibody distribution in rat brain after intranasal administration with MMP-9 pretreatment. Intranasal administration of $^{125}$I-labeled non-targeted rat IgG (~60 µg) to rats with intranasal MMP-9 pretreatment (100 nM). Representative sagittal sections (300 µm) were studied at (A) a medial location (closer to the midline) or (B) a lateral location (further from the midline). A1 and B1 are autoradiographs corresponding to the gross sections shown in A2 and B2, respectively. As shown in FIG. 13, signal is strongest at the putative brain entry areas from the nasal passages. These images include the ventral olfactory bulb region (double asterisk) and the brainstem areas corresponding to the trigeminal nerve entry zone (arrowhead) and the spinal trigeminal tract/nucleus (arrows). Additional signal is evident throughout the brain, particularly on the dorsal surface of the cerebral cortex (asterisk), presumed to correspond to perivascular space signal associated with blood vessels.

FIG. 14 is a set of coronal autoradiographs images showing $^{125}$I-labeled IgG antibody distribution in rat brain after intranasal administration with MMP-9 pretreatment. A0 is a schematic image of rat brain atlas adapted from Paxinos & Watson, 2007. Intranasal administration of $^{125}$I-labeled non-targeted rat IgG (~60 µg) to rats with intranasal MMP-9 pretreatment (100 nM). Representative coronal sections (300 µm) through the olfactory bulbs (A1 and A2), olfactory tracts (B1 and B2), midbrain (C) or pons (D). For A1 and A2, signal intensity is strongest in the ventral olfactory bulb, near the area of olfactory nerve entry from the nasal passages (arrows). Lateral signal is sometimes seen (asterisk) and presumed to correspond to perivascular space signal associated with cerebral blood vessels. For B1 and B2, signal intensity is highest within the rhinal fissure (arrows), presumed to correspond to perivascular space signal associated with blood vessels. Other surface signal may also correspond to perivascular space signal (asterisk). For C, strongest signal was observed in the ventromedial area of the midbrain, in the approximate location of the basilar artery (presumed to be perivascular). For D, autoradiograph is compared with superimposed schematic of section. Strongest signal is associated with an area near to the trigeminal nerve root entry (arrow) and the spinal trigeminal tract (sp5) as well as the ventromedial area in the location of the basilar artery (asterisk).

FIG. 15 is a set of autoradiograph images showing that MMP-9 facilitated delivery of intranasally applied [$^{125}$I]-IgG antibody (150 kDa) to the CNS. A and B were observed at olfactory bulbs (coronal sections). C and D were observed at caudo-putamen level (coronal sections+1 mm from bregma). E was observed at sagittal whole brain (~2.5 mm lateral). The autoradiographs were observed following intranasal administration of tracer levels IgG (72 µCi) with intranasal MMP-9 pre-treatment. These observations show widespread delivery of the antibody. The concentrations of the antibody were in the range of about 10 pM to 100 pM approximately 30 minutes after start of administration.

Example 5

MMP-9 Facilitated Access to Perivascular Spaces Enhances Intranasal Delivery of IgG Antibody (150 Kda) to the CNS. FIG. 16 is a set of images showing that MMP-9 facilitated access to perivascular spaces enhances intranasal delivery of IgG antibody (150 kDa) to the CNS. Alexa-fluor 594-labeled immunoglobulin G (Af594 IgG; 150 kDa) was used as an example of antibodies or antibody fragments. Images A and B were observed on the location of olfactory epithelium. Image A showed that in the absence of MMP-9, Af594 IgG was mainly present on the surface of olfactory epithelium. Image B showed that after the MMP-9 pre-treatment, Af594 IgG was present on the surface of the olfactory epithelium but also diffusely present beneath the olfactory epithelium in the lamina propria and surrounding putative perivascular/perineural spaces in the lamina propria. C shows schematic diagram of the location of frontal pole/olfactory tract. D, E and F show fluorescence images on the location of frontal pole/olfactory tract. These observations suggest: (i) bulk flow along cerebral perivascular spaces is at least partly responsible for rapid distribution of macromolecules within the CNS after intranasal administration and (ii) MMP-9 pretreatment provides a new strategy for non-invasively delivering macromolecules as large as antibodies or antibody fragments to the brain. These observations further demonstrate that cerebral perivascular spaces allow macromolecules to directly access the central nervous system and rapidly achieve widespread distribution following intranasal delivery and MMP-9 facilitates the delivery of macromolecules to the central nervous system following intranasal delivery, possibly by increasing the permeability of the nasal epithelial barrier.

REFERENCE LIST

1. Bauvois, B. (2012). "New facets of matrix metalloproteinases MMP-2 and MMP-9 as cell surface transducers: outside-in signaling and relationship to tumor progression." Biochim Biophys Acta 1825(1): 29-36.
2. Chen, P. and W. C. Parks (2009). "Role of matrix metalloproteinases in epithelial migration." J Cell Biochem 108 (6): 1233-1243.
3. Deli, M. A. (2009). "Potential use of tight junction modulators to reversibly open membranous barriers and improve drug delivery." Biochim Biophys Acta 1788(4): 892-910.
4. Feng, S., J. Cen, et al. (2011). "Matrix metalloproteinase-2 and -9 secreted by leukemic cells increase the permeability of blood-brain barrier by disrupting tight junction proteins." PLoS One 6(8): e20599.
5. Hillery, A. M., A. W. Lloyd, et al., Eds. (2001). Drug Delivery and Targeting for Pharmacists and Pharmaceutical Scientists. Boca Raton, CRC Press.
6. Ilium, L. (2012). "Nasal drug delivery—Recent developments and future prospects." J Control Release, 161(2): 254-263.
7. Lochhead, J. J. and R. G. Thorne (2012). "Intranasal delivery of biologics to the central nervous system." Adv Drug Deliv Rev 64(7): 614-628.
8. Maskos, K. and W. Bode (2003). "Structural basis of matrix metalloproteinases and tissue inhibitors of metalloproteinases." Mol Biotechnol 25(3): 241-266.
9. Rosenberg, G. A. (2009). "Matrix metalloproteinases and their multiple roles in neurodegenerative diseases." Lancet Neurol 8(2): 205-216.
10. Rosenberg, G. A. (2012). "Neurological diseases in relation to the blood-brain barrier." J Cereb Blood Flow Metab.
11. Rosenberg, G. A., E. Y. Estrada, et al. (1998). "Matrix metalloproteinases and TIMPs are associated with blood-brain barrier opening after reperfusion in rat brain." Stroke 29(10): 2189-2195.
12. Roy, R., J. Yang, et al. (2009). "Matrix metalloproteinases as novel biomarkers and potential therapeutic targets in human cancer." J Clin Oncol 27(31): 5287-5297.
13. Thorne, R. G., C. R. Emory, et al. (1995). "Quantitative analysis of the olfactory pathway for drug delivery to the brain." Brain Res 692(1-2): 278-282.
14. Thorne, R. G. and W. H. Frey, 2nd (2001). "Delivery of neurotrophic factors to the central nervous system: pharmacokinetic considerations." Clin Pharmacokinet 40(12): 907-946.
15. Thorne, R. G., L. R. Hanson, et al. (2008). "Delivery of interferon-beta to the monkey nervous system following intranasal administration." Neuroscience 152(3): 785-797.
16. Thorne, R. G., G. Pronk, et al. (2000). "Delivery of insulin-like growth factor-1 to the brain and spinal cord along olfactory and trigeminal pathways following intranasal administration: a noninvasive method for bypassing the blood-brain barrier." Society for Neuroscience Abstracts 26(2): 1365.
17. Thorne, R. G., G. J. Pronk, et al. (2004). "Delivery of insulin-like growth factor-I to the rat brain and spinal cord along olfactory and trigeminal pathways following intranasal administration." Neuroscience 127(2): 481-496.
18. Tsukatani, T., H. L. Fillmore, et al. (2003). "Matrix metalloproteinase expression in the olfactory epithelium." Neuroreport 14(8): 1135-1140.
19. Vermeer, P. D., J. Denker, et al. (2009). "MMP9 modulates tight junction integrity and cell viability in human airway epithelia." Am J Physiol Lung Cell Mol Physiol 296(5): L751-762.
20. Van den Steen, P. E., Dubois, B., et al. (2002). "Biochemistry and Molecular Biology of Gelatinase B or Matrix Metalloproteinase-9 (MMP-9)." Critical Reviews in Biochemistry and Molecular Biology 37(6): 375-536.
21. Oskar Adolfsson, Maria Pihlgren, Nicolas Toni, Yvan Varisco, Anna Lucia Buccarello, Katia Antoniello, Sophie Lohmann, Kasia Piorkowska, Valerie Gafner, Jasvinder K. Atwal, Janice Maloney, Mark Chen, Alvin Gogineni, Robby M. Weimer, Deborah L. Mortensen, Michel Friesenhahn, Carole Ho, Robert Paul, Andrea Pfeifer, Andreas Muhs, and Ryan J. Watts, "An Effector-Reduced Anti-β-Amyloid (Aβ) Antibody with Unique Aβ Binding Properties Promotes Neuroprotection and Glial Engulfment of Aβ." The Journal of Neuroscience, Jul. 11, 2012•32(28): 9677-9689
22. Shyeilla V. Dhuria, Leah R. Hanson, and William H. Frey, "Novel Vasoconstrictor Formulation to Enhance Intranasal Targeting of Neuropeptide Therapeutics to the Central Nervous System." The Journal of Pharmacology and Experimental Therapeutics, 2009, 328:312-320.

We claim:

1. A method for delivering an active compound to a patient comprising the steps of:
   (a) administering intranasally a therapeutically effective amount of MMP-9 or a functionally equivalent fragment to the patient, and
   (b) enhancing intranasal delivery of an active compound by administering intranasally the active compound to the patient,
   wherein after the step (a) the tight junctions of the patient's nasal epithelial cells are modulated or wherein the basal lamina of the patient is partially digested and type IV collagen of the patient is degraded or wherein access to the patient's perineural, perivascular, or lymphatic compartment spaces is facilitated, and wherein MMP-9 or a functionally equivalent fragment facilitates the active compound access to the cranial nerves of the patient.

2. The method according to claim 1, wherein step (a) and step (b) are simultaneous.

3. The method according to claim 1, wherein step (b) is subsequent to step (a).

4. The method according to claim 1, wherein step (b) is within 5 minutes to 1 hour after step (a).

5. The method according to claim 1, wherein step (b) is within 4 hours after step (a).

6. The method according to claim 1, wherein step (a) comprises a preparation of MMP-9 or a functionally equivalent fragment solution having a concentration of 1 nanomolar to 4000 nanomolar.

7. The method according to claim 1, wherein step (a) comprises a preparation of MMP-9 or a functionally equivalent fragment solution having a concentration of 1 nanomolar to 400 nanomolar.

8. The method according to claim 7, wherein the concentration of MMP-9 or a functionally equivalent fragment is between 1 nanomolar and 150 nanomolar.

9. The method according to claim 1, wherein the active compound includes any or a combination of biopharmaceuticals, macromolecules, and therapeutic agents.

10. The method according to claim 9, wherein biopharmaceuticals are selected from antibodies or antibody fragments, peptides, proteins, and stem cells and wherein macromolecules are selected from RNA, asRNA, siRNA, DNA, cDNA, and any other oligonucleotides.

11. The method according to claim 1, wherein the active compound comprises antibodies or antibody fragments.

12. A method for treating a patient suffering from a condition in need of MMP-9 or a functionally equivalent fragment comprising the steps of:
(a) providing a solution of MMP-9 or a functionally equivalent fragment, and
(b) treating the patient intranasally with a therapeutically effective amount of MMP-9 or a functionally equivalent fragment solution, wherein the tight junctions of the patient's nasal epithelial cells are modulated or wherein the basal lamina of the patient is partially digested and type IV collagen of the patient is degraded or wherein the patient's access to perineural, perivascular, or fila olfactoria compartment spaces is facilitated.

13. The method according to claim 12, wherein the solution of MMP-9 or a functionally equivalent fragment is a solution having a concentration between 1 nanomolar and 400 nanomolar.

* * * * *